US011948230B2

(12) United States Patent
Antoniades et al.

(10) Patent No.: US 11,948,230 B2
(45) Date of Patent: Apr. 2, 2024

(54) METHOD FOR PREDICTING CARDIOVASCULAR RISK

(71) Applicant: Oxford University Innovation Limited, Botley (GB)

(72) Inventors: Charalambos Antoniades, Headington (GB); Keith Channon, Headington (GB); Evangelos Oikonomou, Headington (GB); Stefan Neubauer, Headington (GB)

(73) Assignee: Oxford University Innovation Limited, Botley (GB)

( * ) Notice: Subject to any disclaimer, the term of this patent is extended or adjusted under 35 U.S.C. 154(b) by 0 days.

(21) Appl. No.: 18/062,829

(22) Filed: Dec. 7, 2022

(65) Prior Publication Data

US 2023/0113005 A1    Apr. 13, 2023

Related U.S. Application Data

(62) Division of application No. 17/454,540, filed on Nov. 11, 2021, which is a division of application No. (Continued)

(30) Foreign Application Priority Data

Oct. 31, 2016 (GR) ............................. 20160100555
Dec. 2, 2016 (GB) ................................... 1620494

(51) Int. Cl.
   *G06T 11/00* (2006.01)
   *A61B 6/00* (2006.01)
   (Continued)

(52) U.S. Cl.
   CPC ............ *G06T 11/008* (2013.01); *A61B 6/032* (2013.01); *A61B 6/504* (2013.01); *A61B 6/5217* (2013.01);
   (Continued)

(58) Field of Classification Search
   CPC ....... G06T 11/008; G06T 7/62; G06T 7/0012; G06T 2207/30048; G06T 2207/10081;
   (Continued)

(56) References Cited

U.S. PATENT DOCUMENTS

11,393,137 B2    7/2022 Antoniades et al.
2010/0278405 A1  11/2010 Kakadiaris et al.
(Continued)

FOREIGN PATENT DOCUMENTS

WO   WO 2006/055498       5/2006
WO   WO 2015/073977 A1    5/2015
(Continued)

OTHER PUBLICATIONS

Lu et al. 2016 Atherosclerosis 251:47-54 (Year: 2016).*
(Continued)

*Primary Examiner* — Keith M Raymond
*Assistant Examiner* — Patrick M Mehl
(74) *Attorney, Agent, or Firm* — Knobbe, Martens, Olson & Bear, LLP

(57) ABSTRACT

The present invention describes a new functional biomarker of vascular inflammation and its use in predicting all-cause or cardiac mortality. The invention also provides a method for stratifying patients according to their risk of all-cause or cardiac mortality using data gathered from a computer tomography scans of a blood vessel to determine a specific combination of structural and functional biomarkers of vascular inflammation and disease.

11 Claims, 9 Drawing Sheets

Related U.S. Application Data

16/345,165, filed as application No. PCT/GB2017/053262 on Oct. 31, 2017, now Pat. No. 11,393,137.

(51) Int. Cl.
| | |
|---|---|
| *A61B 6/03* | (2006.01) |
| *A61B 6/50* | (2024.01) |
| *G06T 7/00* | (2017.01) |
| *G06T 7/62* | (2017.01) |
| *G16H 30/40* | (2018.01) |
| *G16H 50/30* | (2018.01) |

(52) U.S. Cl.
CPC .............. *G06T 7/0012* (2013.01); *G06T 7/62* (2017.01); *G16H 30/40* (2018.01); *G16H 50/30* (2018.01); *G06T 2207/10081* (2013.01); *G06T 2207/30048* (2013.01); *G06T 2207/30101* (2013.01)

(58) Field of Classification Search
CPC . G06T 2207/30101; G06T 7/00; G16H 50/30; G16H 30/40; A61B 6/504; A61B 6/5217; A61B 6/03; Y02A 90/10
See application file for complete search history.

(56) References Cited

U.S. PATENT DOCUMENTS

| | | | |
|---|---|---|---|
| 2012/0078099 | A1 | 3/2012 | Suri |
| 2012/0243764 | A1 | 9/2012 | Dey et al. |
| 2016/0109458 | A1 | 4/2016 | Ferrari et al. |
| 2019/0287276 | A1* | 9/2019 | Antoniades .......... A61B 6/5217 |
| 2022/0139005 | A1 | 5/2022 | Antoniades et al. |

FOREIGN PATENT DOCUMENTS

| | | | | |
|---|---|---|---|---|
| WO | WO 2016/024128 | 2/2016 | | |
| WO | WO-2016024128 A1 * | 2/2016 | .............. | A61B 6/032 |

OTHER PUBLICATIONS

Alexopoulos et al. (2013). "Effect of Intensive Versus Moderate Lipid-Lowering Therapy on Epicardial Adipose Tissue in Hyperlipidemic Post-Menopausal Women: A Substudy of the BELLES Trial (Beyond Endorsed Lipid Lowering with EBT Scanning)." J Am Coll Cardiol 61(19): 1956-1961.
Alvey et al. (2014). "Association of Fat Density With Subclinical Atherosclerosis." J Am Heart Assoc 3(4):e000788, pp. 1-8.
Antonopoulos et al, "Detecting human coronary inflammation by imaging perivascular fat", Sci. Transl. Med., vol. 9, eaal2658, Jul. 12, 2017, pp. 1-12.
Bezerra, et al. (2009). "Intracoronary Optical Coherence Tomography: A Comprehensive Review: Clinical and Research Applications." JACC Cardiovasc Interv 2(11): 1035-1046.
Cutlip et al. (2007). "Clinical End Points in Coronary Stent Trials: A Case for Standardized Definitions." Circulation 115(17): 2344-2351.
Fishbein et al. (1996). "How Big Are Coronary Atherosclerotic Plaques That Rupture?" Circulation 94(10): 2662-2666.
Fleg et al. (2012). "Detection of High-Risk Atherosclerotic Plaque: Report of the NHLBI Working Group on Current Status and Future Directions." JACC Cardiovasc Imaging 5(9): 941-955.
Greenland et al. (2004). "Coronary Artery Calcium Score Combined With Framingham Score for Risk Prediction in Asymptomatic Individuals." JAMA 291(2): 210-215.
Hecht et al. (2015). "High-Risk Plaque Features on Coronary CT Angiography." JACC Cardiovasc Imaging 8(11): 1336-1339.
Hell et al. (2016). "CT-based analysis of pericoronary adipose tissue density: Relation to cardiovascular risk factors and epicardial adipose tissue volume." J Cardiovasc Comput Tomogr 10(1): 52-60.
Hell et al. (2016). "Epicardial adipose tissue volume but not density is an independent predictor for myocardial ischemia." J Cardiovasc Comput Tomogr 10(2):141-149.
Hicks et al. (2015). "2014 ACC/AHA Key Data Elements and Definitions for Cardiovascular Endpoint Events in Clinical Trials: A Report of the American College of Cardiology/American Heart Association Task Force on Clinical Data Standards (Writing Committee to Develop Cardiovascular Endpoints Data Standards)." J Am Coll Cardiol 66(4): 403-469.
Huang et al. (2001). "The Impact of Calcification on the Biomechanical Stability of Atherosclerotic Plaques." Circulation 103(8): 1051-1056.
Joshi et al. (2014). "$^{18}$F-fluoride positron emission tomography for identification of ruptured and high-risk coronary atherosclerotic plaques: a prospective clinical trial." Lancet 383: 705-713.
Lee et al. (2016). "Association of Changes in Abdominal Fat and Cardiovascular Risk Factors." J Am Coll Cardiol 68(14): 1509-1521.
Lee et al. (2012). "Evaluating Oxidative Stress in Human Cardiovascular Disease: Methodological Aspects and Considerations." Curr Med Chem 19(16): 2504-2520.
Lu et al. (2016). "Epicardial and Paracardial Adipose Tissue Volume and Attenuation—Association with High-Risk Coronary Plaque on Computed Tomographic Angiography in the ROMICAT II Trial." Atherosclerosis 251: 47-54.
Major et al. (2011), "What Fans the Fire Insights Into Mechanisms of Inflammation in Atherosclerosis and Diabetes Mellitus", Circulation, 124: 2809-2811.
Margaritis et al. (2013). "Interactions Between Vascular Wall and Perivascular Adipose Tissue Reveal Novel Roles for Adiponectin in the Regulation of Endothelial Nitric Oxide Synthase Function in Human Vessels." Circulation 127(22): 2209-2221.
Maurovich-Horvat et al. (2014). "Comprehensive plaque assessment by coronary CT angiography." Nat Rev Cardiol 11(7): 390-402.
McDaniel et al. (2011). "Contemporary Clinical Applications of Coronary Intravascular Ultrasound." JACC Cardiovasc Interv 4(11): 1155-1167.
Obaid et al. (2013). "Atherosclerotic Plaque Composition and Classification Identified by Coronary Computed Tomography: Assessment of Computed Tomography-Generated Plaque Maps Compared With Virtual Histology Intravascular Ultrasound and Histology." Circ Cardiovasc Imaging 6(5): 655-664.
Okayama et al. (2012). "The Influence of Effective Energy on Computed Tomography Number Depends on Tissue Characteristics in Monoenergetic Cardiac Imaging." Radiol Res Pract 2012: 150980, 7 pages.
Pracon et al., "Epicardial Adipose Tissue Radiodensity Is Independently Related to Coronary Atherosclerosis—A Multidetector Computed Tomography Study", Circulation Journal Official Journal of the Japanese Circulation Society, vol. 75, Feb. 2011, pp. 391-397.
Rodriguez-Granillo et al., "Defining the non-vulnerable and vulnerable patients with computed tomography coronary angiography: evaluation of atherosclerotic plaque burden and composition", European Heart Journal—Cardiovascular Imaging (2016) vol. 17, pp. 481-491.
Rogers et al. (2011). "Imaging of Coronary Inflammation with FDG-PET: Feasibility and Clinical Hurdles." Curr Cardiol Rep 13(2): 138-144.
Rosenquist et al. (2013). "Visceral and Subcutaneous Fat Quality is Associated with Cardiometabolic Risk." JACC Cardiovasc Imaging 6(7): 762-771.
Ross, R., (1999) "Atherosclerosis—An Inflammatory Disease", The New England Journal of Medicine, vol. 340, No. 2, pp. 115-126.
Saremi et al. (2015). "Coronary Plaque Characterization Using CT." AJR Am J Roentgenol 204(3): W249-260.
Tamarappoo et al. (2010). "Increased Pericardial Fat Volume Measured From Noncontrast CT Predicts Myocardial Ischemia by SPECT." JACC Cardiovasc Imaging 3(11): 1104-1112.
Weintraub et al. (2000). "C-reactive protein, inflammation and atherosclerosis: do we really understand it yet?" Eur Heart J 21(12): 958-960.

(56) References Cited

OTHER PUBLICATIONS

Yamashita et al., "Association between increased epicardial adipose tissue vol. and coronary plaque composition", Heart Vessels (2014) vol. 29, pp. 569-577.
International Search Report and Written Opinion for PCT/GB2017/053262 dated Dec. 13, 2017 in 14 pages.
Search Report for GB 1620494.3 dated Jun. 2, 2018 in 4 pages.

* cited by examiner (A) 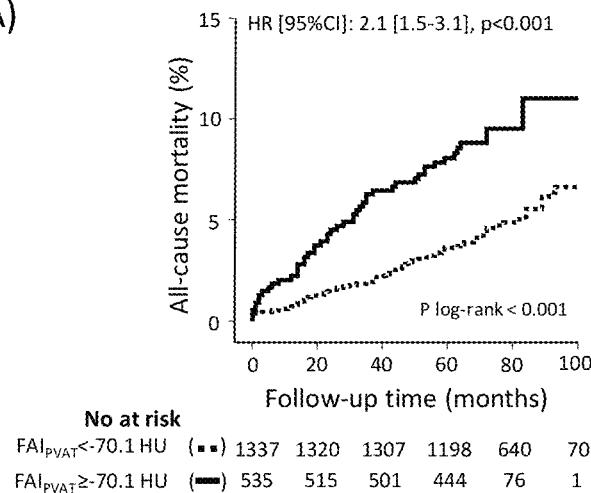
(B) 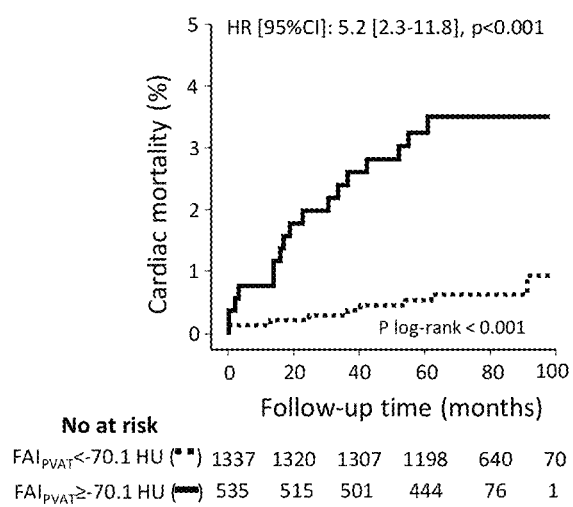
(C) 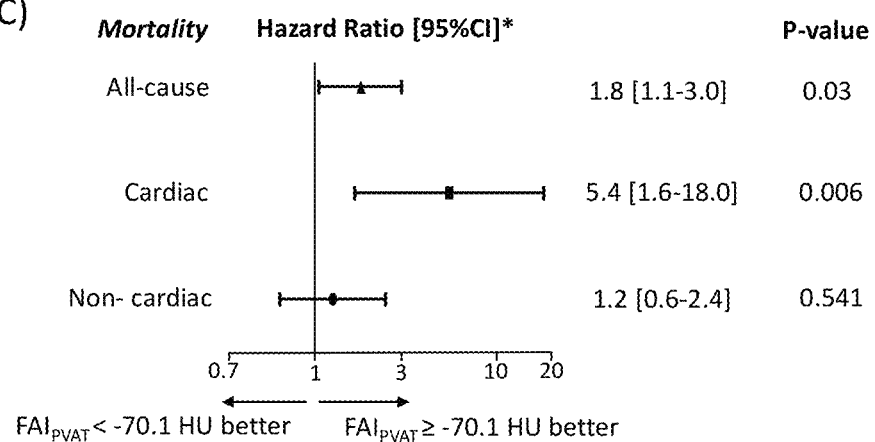
FIGURE 5

(A) The Oxford Integrated Cardiac CT score (OxScore)
A novel CTA-based scoring system for mortality risk stratification

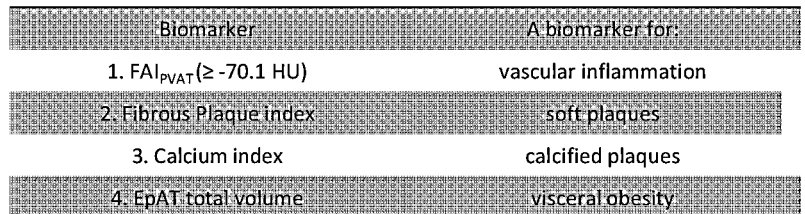

| Biomarker | A biomarker for: |
|---|---|
| 1. $FAI_{PVAT}$ ($\geq -70.1$ HU) | vascular inflammation |
| 2. Fibrous Plaque index | soft plaques |
| 3. Calcium index | calcified plaques |
| 4. EpAT total volume | visceral obesity |

OxScore = The individualized probability for all-cause OR cardiac mortality over 6.4 years OxScore (%) = $100 \ast 10^y/(1+10^y)$
where y = $c + a \ast FAI_{PVAT} + b \ast EpAT\text{-}vol + d \ast FPi + e \ast Calcium\text{-}i$ a, b, d, e = beta coefficients and c = constant calculated on logistic regression with:
$FAI_{PVAT}$ (=1 if $\geq -70.1$ HU and 0 if $< -70.1$ HU), FPi, Calcium-i, EpAT volume (in cm³) as the independent
<u>and</u> all-cause OR cardiac mortality as the dependent variables.

Mortality risk stratification based on the OxSCORE

All-cause mortality            Cardiac mortality (B) 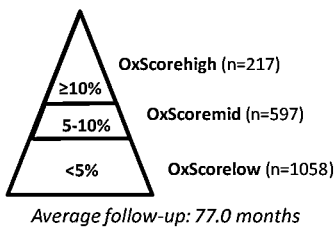   (C) 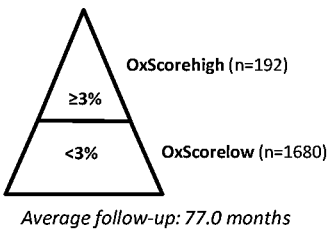

≥10% OxScorehigh (n=217)
5-10% OxScoremid (n=597)
<5% OxScorelow (n=1058)
*Average follow-up: 77.0 months*

≥3% OxScorehigh (n=192)
<3% OxScorelow (n=1680)
*Average follow-up: 77.0 months*

(D) 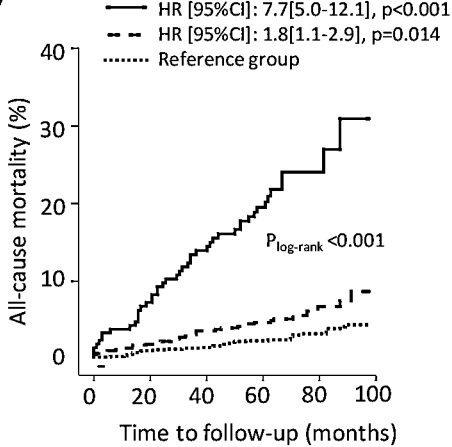   (E) 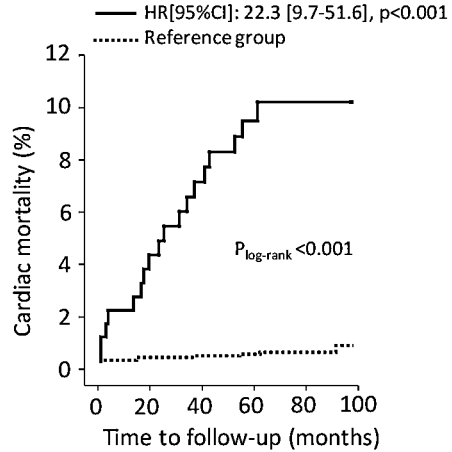

HR [95%CI]: 7.7[5.0-12.1], p<0.001
HR [95%CI]: 1.8[1.1-2.9], p=0.014
Reference group
$P_{log\text{-}rank} < 0.001$ HR[95%CI]: 22.3 [9.7-51.6], p<0.001
Reference group
$P_{log\text{-}rank} < 0.001$ No at risk
OxScorelow ........ 1059 1047 1043 969 507 56
OxScoremid — — 596 586 576 515 171 13
OxScorehigh ——— 217 202 189 158 38 2

No at risk
OxScorelow ····· 1680 1658 1641 1497 680 70
OxScorehigh —— 192 177 167 145 36 1

FIGURE 6

Total mortality

(A)

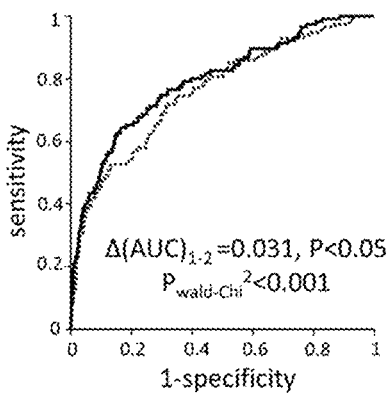

Model 1: AUC = 0.76 [0.711-0.808], p<0.001
Model 2: AUC = 0.791 [0.744-0.837], p<0.001

$\Delta(AUC)_{1-2} = 0.031$, $P<0.05$
$P_{wald-Chi}^2 < 0.001$ (B)

| All-cause mortality risk | | Model 1 | | |
|---|---|---|---|---|
| | | <5% | ≥5% | Any |
| Model 2: Model 1 + OxScore | <5% | 2.2% (24/1014) | 1.6% (3/191) | 3.1% (27/1205) |
| | ≥5% | 4.6% (5/109) | 11.1% (82/558) | 10.5% (87/667) |
| | Any | 2.4% (29/1123) | 9.0% (85/749) | 6.1% (114/1872) |

NRI = 7.6 % average follow-up: 77 ± 14.2 months

Cardiac mortality

(C)

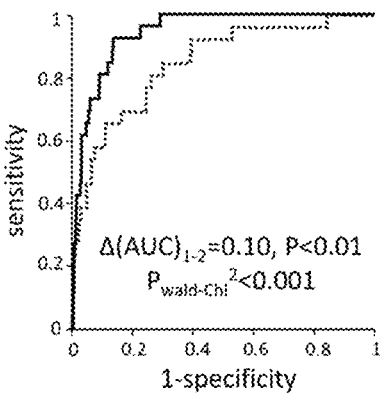

Model 1: AUC = 0.846 [0.769-0.923], p<0.001
Model 2: AUC = 0.946 [0.917-0.974], p<0.001

$\Delta(AUC)_{1-2} = 0.10$, $P<0.01$
$P_{wald-Chi}^2 < 0.001$ (D)

| Cardiac mortality risk | | Model 1 | | |
|---|---|---|---|---|
| | | <3% | ≥3% | Any |
| Model 2: Model 1 + OxScore | <3% | 0.4% (6/1610) | 6.6% (5/76) | 0.5% (11/1686) |
| | ≥3% | 0.4% (1/91) | 14.7% (14/95) | 8.1% (15/186) |
| | Any | 0.4% (7/1701) | 11.1% (19/171) | 1.4% (26/1872) |

NRI = 11.3 % average follow-up: 77 ± 14.2 months

FIGURE 7

METHOD FOR PREDICTING CARDIOVASCULAR RISK

CROSS-REFERENCE TO RELATED APPLICATIONS

This application is a divisional of U.S. patent application Ser. No. 17/454,540 filed on Nov. 11, 2021, which is a divisional of U.S. patent application Ser. No. 16/345,165 filed on Apr. 25, 2019, which is the U.S. National Stage under 35 U.S.C. § 371 of PCT App. No. PCT/GB2017/053262 filed on Oct. 31, 2017, which in turn claims the benefit of GB Patent App. No. 1620494.3 filed on Dec. 2, 2016 and GR Patent App. No. 20160100555 filed on Oct. 31, 2016. Each of the foregoing applications is hereby incorporated by reference in their entireties.

FIELD OF THE INVENTION

The present invention relates to novel biomarkers of cardiovascular risk and methods for predicting all-cause mortality and cardiac events, including cardiac mortality.

BACKGROUND OF THE INVENTION

Atherosclerosis is a progressive process in which an artery wall thickens as a result of invasion and accumulation of white blood cells. This inflammatory process results in plaques within the vessel wall containing living white blood cells, dead cell debris and fatty deposits including cholesterol and triglycerides.

Stable atherosclerotic plaques, which tend to be asymptomatic, are typically rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap eventually induce clot formation in the lumen, and such clots can block arteries or detach, move into the circulation and eventually block smaller downstream vessels causing thromboembolism. Chronically expanding plaques are frequently asymptomatic until vessel occlusion (stenosis) is severe enough that blood supply to downstream tissue is insufficient.

Atherosclerosis is asymptomatic for decades because the arteries enlarge at all plaque locations and blood flow is not immediately affected. Indeed, plaque ruptures are also asymptomatic unless they result in sufficient narrowing or closure of an artery that impedes blood flow to different organs so as to induce symptoms. Typically, the disease is only diagnosed when the patient experiences other cardiovascular disorders such as stroke or heart attack. Symptomatic atherosclerosis is typically associated with men in their 40s and women in their 50s to 60s. Sub-clinically, the disease begins to appear in childhood, and noticeable signs can begin developing at puberty. While coronary artery disease is more prevalent in men than women, atherosclerosis of the cerebral arteries and strokes equally affect both sexes.

Atherosclerosis may cause narrowing in the coronary arteries, which are responsible for bringing oxygenated blood to the heart, and this can produce symptoms such as the chest pain of angina, shortness of breath, sweating, nausea, dizziness or light-headedness, breathlessness or palpitations. Cardiac arrhythmias may also result from cardiac ischemia. Atherosclerosis that causes narrowing in the carotid arteries, which supply blood to the brain and neck, can produce symptoms such as a feeling of weakness, not being able to think straight, difficulty speaking, becoming dizzy and difficulty in walking or standing up straight, blurred vision, numbness of the face, arms, and legs, severe headache and losing consciousness. These symptoms may also be present in stroke, which is caused by marked narrowing or closure of arteries going to the brain leading to brain ischemia and death of cells in the brain. Peripheral arteries, which supply blood to the legs, arms, and pelvis may also be affected. Symptoms can include numbness within the affected limbs, as well as pain. Plaque formation may also occur in the renal arteries, which supply blood to the kidneys. Plaque occurrence and accumulation leads to decreased kidney blood flow and chronic kidney disease, which, like all other areas, are typically asymptomatic until late stages.

Vascular inflammation is a key feature in atherogenesis and plays a critical role in atherosclerotic plaque stability by triggering plaque rupture leading to acute coronary syndromes (see Ross R. N Engl J Med 1999; 340:115-26, and Major A S et al Circulation 2011; 124:2809-11). Importantly, more than 50% of acute coronary syndromes are caused by highly inflamed but anatomically non-significant atherosclerotic plaques (Fishbein M C et al. Circulation 1996; 94:2662-6), which are not identifiable by any of the existing clinical diagnostic tests.

Early, non-invasive diagnosis of vascular inflammation has been hailed as the "holy grail" of cardiovascular diagnostics and could help improve risk stratification in primary and secondary prevention. However, the current state-of-the-art methods for the diagnosis of vascular inflammation and cardiovascular risk prediction are suboptimal and have several limitations. Circulating inflammatory biomarkers (e.g. CRP, TNF-α) have a limited value in cardiovascular risk prediction since they are not specific to the cardiovascular system and have poor correlation with local vascular inflammation (see Weintraub et al. Eur Heart J 2000; 21:958-60; Lee R et al. Current medicinal chemistry 2012; 19:2504-20; and Margaritis M et al. Circulation 2013; 127:2209-21).

In the field of cardiovascular imaging, the predictive value of Agatston coronary calcium score measured by CT has been long-established. However, coronary calcification represents a non-reversible process that does not change in response to appropriate medical therapy (e.g. statins) (Alexopoulos N et al. Journal of the American College of Cardiology 2013; 61:1956-61). In fact, calcified plaques are considered more stable and less likely to rupture compared to plaques with high-risk features, such as a thin-cap fibroatheromas and a large necrotic core (Huang H et al. Circulation 2001; 103:1051-6). Detection of high-risk plaque features such as microcalcification, a large necrotic core or positive remodelling on CT angiograms have all been shown to predict future cardiac events (Hecht H S et al. JACC Cardiovasc Imaging 2015; 8:1336-9; and Saremi F et al. AJR Am J Roentgenol 2015; 204:W249-60), but the reliability of the method is affected by the observer's expertise and CT settings and parameters, including spatial resolution (Maurovich-Horvat P et al. Nat Rev Cardiol 2014; 11:390-402; and Fleg J L et al. JACC Cardiovasc Imaging 2012; 5:941-55).

Newer invasive methods such as optical coherence tomography (OCT) and intravascular ultrasound (IVUS) have been more successful in detecting high-risk plaques but are invasive, expensive, carry a small yet significant risk of in-procedure complications (Bezerra H G et al. JACC Cardiovasc Interv 2009; 2:1035-46; and McDaniel M C et al. JACC Cardiovasc Interv 2011; 4:1155-67), and are therefore not eligible for primary prevention and wide screening of low-risk individuals. Positron emission tomography (PET) with $^{18}$F-FDG is expensive, associated with significantly higher levels of radiation exposure compared to CT alone, not readily available and limited by myocardial uptake of the radiotracer that results in significant background noise (Joshi N V et al. Lancet 2014; 383:705-13; and Rogers I S et al. Curr Cardiol Rep 2011; 13:138-44). Even the introduction of newer radiotracers (such as $^{18}$F—NaF), although promising, carries many of the limitations of traditional PET imaging, including but not limited to significant radiation exposure, limited availability and no demonstrated value in primary or even secondary prevention (Joshi N V et al. Lancet 2014; 383:705-13).

Perivascular adipose tissue (PVAT) surrounds (coronary) arteries and may be involved in local stimulation of atherosclerotic plaque formation. PVAT can be quantified using a number of techniques, including for example, echocardiography, computed tomography (CT) and magnetic resonance imaging (MRI). The quantity of PVAT correlates with some parameters of metabolic syndrome including increased waist circumference, hypertriglyceridemia and hyperglycemia, and with coronary atherosclerosis. PVAT has long been known to secrete pro-inflammatory proteins and induce inflammation of the artery wall. The long-held understanding of the pathology of atherogenesis in the vascular wall was that it is stimulated externally, and it was suggested that PVAT played a key role in this process.

It has recently become clear that vascular inflammation and oxidative stress has the ability to affect the biology of PVAT as the vascular wall releases mediators able to exert a paracrine effect on the neighbouring PVAT (see e.g. Margaritis et al. Circulation 2013; 127(22):2209-21). This observation was in contrast to the classical theory according to which PVAT sends paracrine signals to the vascular wall. It is now understood that the biology of PVAT is shaped by signals received from the blood vessel it surrounds, and characterisation of PVAT can provide useful information regarding the biology and health of that blood vessel.

In WO2016/024128 it was demonstrated that the quantified radiodensity of perivascular tissue ($QR_{PVAT}$), which is also known as and referred to herein as the fat attenuation index of perivascular tissue ($FAI_{PVAT}$), is positively associated with the presence of coronary artery disease (CAD) and the volume of fibrous plaque in the proximal RCA independently of the presence of coronary calcium. As part of the same study, the present inventors also showed that $FAI_{PVAT}$ changes in a dynamic way in response to local rupture of a culprit lesion in patients with acute MI and can distinguish culprit from non-culprit lesions. These observations supported the inventors' hypothesis that $FAI_{PVAT}$ could function as a dynamic biomarker of vascular inflammation and cardiovascular risk and offer diagnostic and prognostic information beyond that of traditional biomarkers, such as coronary calcium.

However, there remains an urgent need for the identification and development of functional biomarkers that will describe vascular inflammation, rather than structural and non-reversible changes in the vascular wall, and diagnostic tools to aid non-invasive detection of vascular inflammation and enable stratification of patients who are at risk of suffering serious cardiac events.

SUMMARY OF THE INVENTION

According to a first aspect, the present invention provides a method for determining the perivascular water index (PVWi) of a blood vessel, comprising (i) using data gathered from a computer tomography scan along a length of the vessel to determine the total volume of voxels of water within an attenuation window around the attenuation of water within the perivascular space a pre-determined distance from the outer wall of the vessel, and (ii) correcting the total volume of the voxels of water for the size of the vessel by dividing the total volume of voxels of water determined in step (i) by the total perivascular volume.

According to a second aspect, the present invention is directed to the use of perivascular water index (PVWi), as defined according to the method of the first aspect of the invention, as a functional biomarker of vascular inflammation. According to this aspect, PVWi can be used alone, or in combination with one or more other biomarkers, to predict all-cause or cardiac mortality risk in a patient. In particular, PVWi can be used in combination with one or more of calcium index, fibrous plaque index, fat attenuation index of the perivascular adipose tissue, volumetric perivascular characterisation index, fat attenuation index and total volume of the epicardial adipose tissue to predict all-cause or cardiac mortality risk in a patient.

According to a third aspect, the present invention provides a method for predicting the risk of a patient suffering a cardiovascular event, said method comprising:
(a) using data gathered from a computer tomography scan along a length of a blood vessel to determine:
(i) calcium index (Calcium-i); and/or
(ii) fibrous plaque index (FPi)
and at least one of
(iii) fat attenuation index of the perivascular adipose tissue ($FAI_{PVAT}$), and/or
(iv) perivascular water index (PVWi), and
with the possible addition of any of the following:
(v) volumetric perivascular characterisation index (VPCI)
(vi) total epicardial adipose tissue volume (EpAT-vol);
(vii) fat attenuation index (FAI) of epicardial adipose tissue ($FAI_{EpAT}$),
(b) comparing each of the values determined in (a) to a pre-determined cut-off value or using the absolute value of each variable in order to generate an output value that indicates the patient's risk of suffering a cardiovascular event.

In a preferred embodiment of the method of the third aspect of the invention, both $FAI_{PVAT}$ and PVWi are determined in step (a) of the method.

In one embodiment, the method according to the third aspect of the invention further comprises determining one or more of (vi) fat attenuation index of total volume of the epicardial adipose tissue (EpAT-vol), (vii) the epicardial adipose tissue ($FAI_{EpAT}$), (viii) age and (ix) gender of the patient.

In certain embodiments, the method according to the third aspect of the invention can be used for non-invasive monitoring of aortic aneurysms and/or carotid plaques.

DESCRIPTION OF THE DRAWINGS

The invention is described with reference to the following Figures, in which:

FIG. 5 shows the predictive value of high $FAI_{PVAT}$ (≥−70.1 HU) for all-cause, cardiac and non-cardiac mortality. In univariate Cox regression analysis, high $FAI_{PVAT}$ was linked to a two-fold increase in the risk of all-cause mortality (A) and a more than five-fold increase in the risk of cardiac death (B) compared to the low $FAI_{PVAT}$ group. More importantly, $FAI_{PVAT}$ remained predictive of both all-cause and cardiac mortality in multivariable cox-regression (Panel C, where HR: hazard ratio from cox regression (for $FAI_{PVAT}$<−70.1 HU vs≥−70 HU)). *adjusted for age, gender, hypertension, hypercholesterolemia, diabetes mellitus, active smoker status, medications (antiplatelets and statins), presence of coronary artery disease, calcium index, Agatston score (≥400 vs<400) and type of CT scanner). Interestingly, the predictive value of $FAI_{PVAT}$ appears to be specific for cardiac rather than non-cardiac mortality, suggesting that the new biomarker describes a cardiac-specific biology and that it provides additional information, beyond that of traditional risk factors and biomarkers used in cardiac risk stratification. CAD: Coronary Artery Disease; $FAI_{PVAT}$: Fat Attenuation Index of Perivascular Adipose Tissue; HU: Hounsfield units.

FIG. 6 shows mortality and cardiac risk-stratification based on the OxScore. A novel predictive model was constructed based on four imaging indices that were shown to be strong and independent predictors of all-cause and cardiac mortality in multivariable Cox regression analysis (A). These were $FAI_{PVAT}$, a novel marker of coronary inflammation, fibrous plaque index, a biomarker of soft plaques, calcium index, an imaging index of local calcium deposition in the proximal right coronary artery and finally epicardial adipose tissue (EpAT) volume, an established index of epicardial/visceral adiposity. Based on a logistic regression model, the individual probabilities of all-cause/cardiac mortality were calculated and the study population was subsequently reclassified into risk groups as follows: for all-cause mortality: $OxScore_{high}$: ≥10%, $OxScore_{mid}$: 5-10%, $OxScore_{low}$: <5% (B) and for cardiac mortality: $OxScore_{high}$: ≥3% versus $OxScore_{low}$: <3% (D). Patients in the $OxScore_{high}$ group for all-cause mortality had an almost eight times higher risk of death during follow-up compared to the $OxScore_{low}$ group (C), whereas those in the high-risk group for cardiac-specific mortality, were more than 22 times more likely to die of cardiac causes compared to the low risk group (E). $FAI_{PVAT}$: Fat Attenuation Index of Perivascular Adipose Tissue; FPi: Fibrous Plaque index; HR: Hazard Ratio; HU: Hounsfield units.

FIG. 7 compares OxScore against traditional risk factors and cardiac CT measurements. In order to examine the predictive value of OxScore beyond age, gender, traditional cardiovascular risk factors and standard interpretation of a cardiac CT scan (presence of new or previously known coronary artery disease or high Agatston score≥400), two different models were constructed as follows. Model 1 included age, gender, hypertension (HTN), hypercholesterolemia, diabetes mellitus, active smoker status, presence of coronary artery disease (CAD), Agatston coronary calcium score (CCS), while Model 2 was created by adding the OxScore variables into Model 1. Interestingly, addition of the OxScore variables into the model significantly improved the predictive value for both all-cause and cardiac specific mortality (Δ[AUC]=0.031, P<0.05 for all-cause and Δ[AUC]=0.10, P<0.01 for cardiac mortality) (A, C). Furthermore, addition of the OxScore improved risk classification compared to the standard model, as shown by an NRI index of 7.6% and 11.3% for all-cause and cardiac mortality respectively (B, D). Notably, OxScore appears to predominantly improve reclassification of non-events, suggesting a potential value for this novel risk scoring system in identifying high-risk individuals among those with already present traditional cardiovascular risk factors. AUC: area under the curve; CAD: coronary artery disease; CT: computed tomography; FPi: Fibrous Plaque index; NRI: net reclassification improvement. NS: non significant.

DETAILED DESCRIPTION OF THE INVENTION

Figure 1:
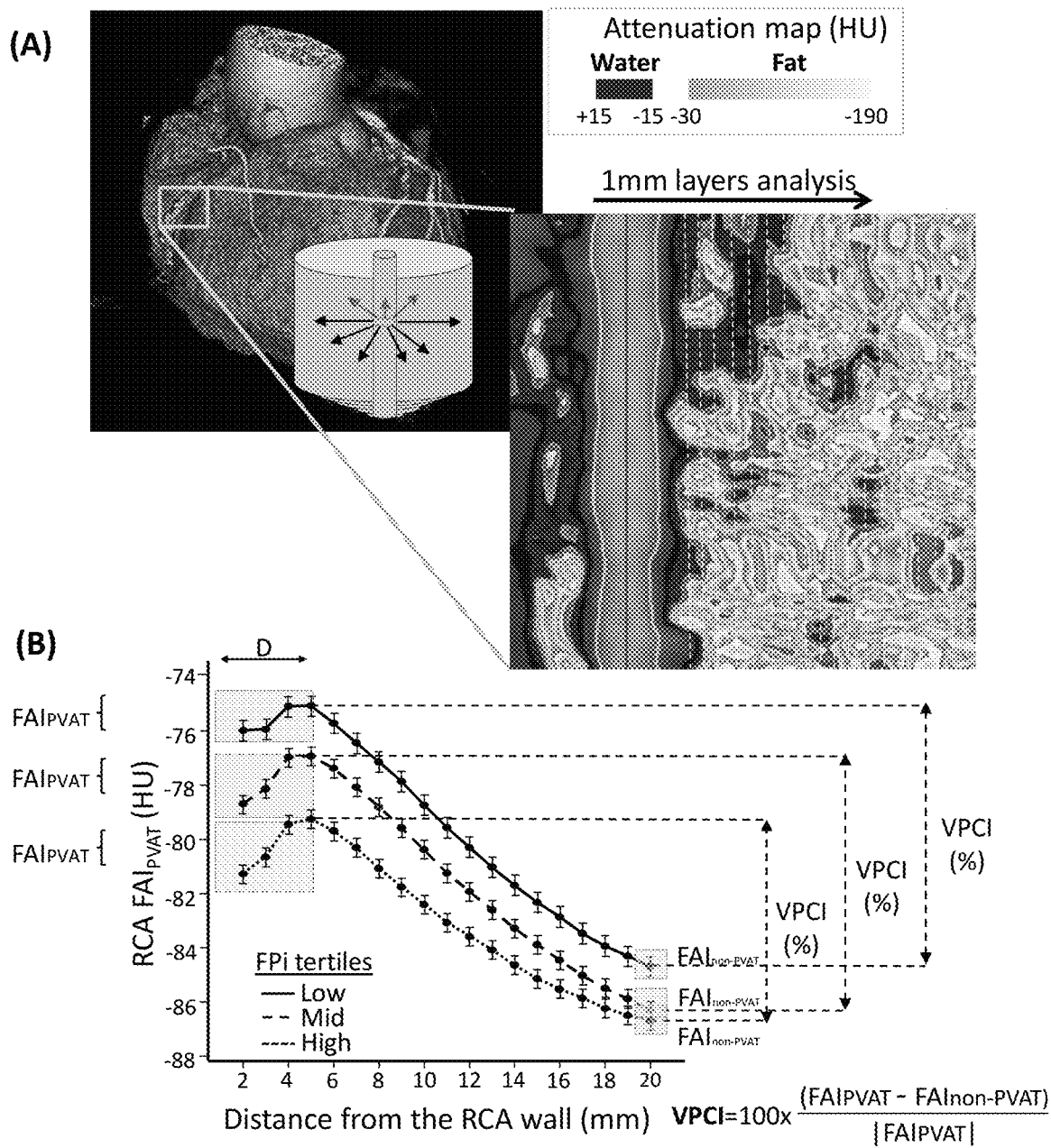
FIG. 1 provides a definition of perivascular adipose tissue (PVAT) indices. (A) Coronary CT angiography images were reconstructed in 3 dimensions. The right coronary artery was tracked and the proximal 10-50 mm of its course were selected on curved multiplanar reconstruction images. The inner and outer walls of the vessel were manually optimized and the perivascular area (up to 20 mm distal to the outer vessel wall) was analysed based on the respective tissue attenuation. A Hounsfield Unit range of −15 to +15 was used to detect perivascular water, whereas a range of −190 to −30 was applied for detection of adipose tissue. (B) The perivascular area was then split in 20 concentric cylindrical layers of 1 mm thickness and fat attenuation index (FAI), defined as the mean attenuation of adipose tissue within the pre-defined range, was then calculated in each layer and plotted against the distance from the vessel wall. PVAT was defined as AT within a radial distance equal to the diameter of the vessel, whereas AT in the most distal layer was defined as non-PVAT. The volumetric perivascular characterization index (VPCI) was then defined as the percent change from $FAI_{PVAT}$ to $FAI_{non-PVAT}$. Further analysis by tertiles of fibrous plaque index (FPi, fibrous plaque volume divided by the total volume of the vessel) revealed a positive association between fibrous plaque burden and FAI of the adipose tissue in the perivascular area. Perivascular Water Index (PVWi) was defined as the total volume of voxels of water within an attenuation window around the attenuation of water (−15 to +15 HU) within the perivascular space a pre-determined distance from the outer wall of the vessel (e.g. a radial distance equal to the diameter of the vessel) divided by the total perivascular volume.

The present inventors have developed a new functional biomarker of vascular inflammation which can be used alone or in combination with other known structural and/or functional biomarkers of vascular inflammation, to predict, with a high degree of accuracy, the risk of a coronary event occurring.

The new functional biomarker of vascular inflammation is a novel index that has been identified by the present inventors, which is referred to herein as "Perivascular Water Index (PVWi)". PVWi is defined as the volume of the voxels within a window above and below the attenuation of water that corresponds to the water content around the inflamed vessel. This biomarker can be used to detect vascular inflammation and/or predict risk of a coronary event occurring on its own, or in combination with other functional or structural biomarkers, as described in detail below.

Therefore, according to a first aspect, the present invention provides a method for determining the perivascular water index (PVWi) of a blood vessel, comprising:
  (i) using data gathered from a computer tomography scan along a length of the vessel to determine the total volume of voxels of water within an attenuation window around the attenuation of water within the perivascular space a pre-determined distance from the outer wall of the vessel, and
  (ii) correcting the total volume of the voxels of water for the volume of the vessel by dividing the total volume of voxels of water determined in step (i) by the total perivascular volume.

The total perivascular volume is defined as the total volume of voxels within a radial distance away from the vascular wall that is representative of the vessel dimensions. For example, the distance may be the diameter of the vessel, or any other aspect that describes the dimensions of the vessel (such as (vessel diameter)/2 or (vessel diameter)×3, or any other subdivision or multiple of a dimension of the vessel.

As used herein, the term "computer tomography scan" refers to a scan generated using computer-processed x-rays to produce tomographic images of specific areas of the scanned perivascular region. The term "computed tomography scan" is synonymous with the terms CT scan and CAT scan. Preferably the CT scan of a blood vessel, or a section thereof, is carried out using routine methods and commercially available instruments.

As used therein, the term "perivascular" refers to the space that surrounds a blood vessel. The term "perivascular tissue" refers to the tissue that surrounds a blood vessel, and may include perivascular adipose tissue (PVAT). The terms "perivascular tissue" and "perivascular space" are used interchangeably herein.

The term "radiodensity" is synonymous with the term "attenuation" and the two terms can be used interchangeably, although the term "attenuation" is preferred.

Attenuation, which is measured in Hounsfield units (HU), is a measure of the relative inability of X-rays to pass through material. Measurement of attenuation values allows tissue types to be distinguished in CT on the basis of their different radio-opacities. Fat is not very radiodense, and it typically measures between −190 and −30 HU while muscle, blood and bone measure between +10 and +40, between +30 and +45, and between +700 and +3000 HU respectively.

In the context of the present invention, an "average" value is understood to mean a central or typical value, and it can be calculated from a sample of measured values using formulas that are widely known and appreciated in the art. Preferably, the average is calculated as the arithmetic mean of the sample of attenuation values, but it can also be calculated as the geometric mean, the harmonic mean, the median or the mode of a set of collected attenuation values. The average value may be calculated by reference to data collected from all voxels within a concentric tissue layer or by reference to a selected population of voxels within the concentric tissue layer, for example water- or adipose tissue-containing voxels.

The term "voxel" has its usual meaning in the art and is a contraction of the words "volume" and "element" referring to each of an array of discrete elements of volume that constitute a notional three-dimensional space.

The term "vascular inflammation" has its usual meaning in the art, and refers to a progressive inflammatory condition characterized by the vascular infiltration by white blood cells, build-up of sclerotic plaques within vascular walls, and in particular, arterial walls. Vascular inflammation is a key process for the initiation and progression of atherosclerosis and vascular disease.

The phrase "conditions associated with vascular inflammation" includes any disease where vascular inflammation is known to play a key role in pathogenesis, such as coronary artery disease, aortic and other vascular aneurysms, carotid plaques, peripheral arterial disease.

In a preferred embodiment of this aspect of the invention, the attenuation window around the attenuation of water is from −30 to +30 Hounsfield units (HU), and more preferably from −15 to +15 HU.

In a preferred embodiment of this aspect of the invention, the pre-determined distance from the outer wall of the vessel referred to in step (i) can be any one of the following three distances:

1. A distance equal to the diameter or radius of the underlying vessel.
2. A distance that is representative of a dimension of the underlying vessel (e.g. any subdivision or multiple of the radius or diameter of the vessel).
3. A standard predetermined distance that is not equal to or related to the diameter of the underlying vessel (e.g. 5 mm).

Preferably, the blood vessel is a coronary blood vessel, such as the aorta. In a preferred embodiment the data is gathered from a computerised tomography scan along a length of the right coronary artery, left anterior descending artery, left circumflex artery, aorta, carotid arteries or femoral arteries. More preferably, the data is gathered from a computerised tomography scan along a 4 cm length, starting 1 cm distally to the origin of the right coronary artery.

For the avoidance of doubt, the methods of the invention utilise CT scan data that has been obtained in vivo, by scanning a living body, but the claimed methods are not practised on the living human or animal body.

PVWi has utility as a functional biomarker of vascular inflammation, and in particular can be used to predict cardiac mortality risk in a patient.

Therefore, a second aspect of the present invention is directed to the use of perivascular water index (PVWi), as defined according to the method of the first aspect of the invention, as a functional biomarker of vascular inflammation.

PVWi may be used alone, or may be used in combination with additional functional and/or structural biomarkers. Preferably, the structural biomarkers include one or more of calcium index (Calcium-i), fibrous plaque index (FPi) or total epicardial adipose tissue volume (EpAT-vol). Preferably, the additional functional biomarkers of vascular inflammation include one or more of the fat attenuation index of the perivascular adipose tissue ($FAI_{PVAT}$), volumetric perivascular characterisation index (VPCI) and epicardial adipose tissue Fat Attenuation Index ($FAI_{EpAT}$).

VPCI is defined as the difference between the quantified attenuation (or radiodensity) of perivascular adipose tissue ($FAI_{PVAT}$) and the quantified attenuation (or radiodensity) of non-perivascular adipose tissue ($FAI_{nPVAT}$). Non-perivascular adipose tissue (nPVAT) is defined as adipose tissue that is located 2 cm or more away from the outer wall of the vessel.

The VPCI and FAI indices are defined and described in detail in the present inventors' earlier patent publication WO2016/024128, the entire contents of which are incorporate by reference. In that publication FAI is referred to as the QR index (but the two are synonymous).

The terms "Fibrous Plaque Index (FPI)" and "(Fibrous) plaque" are synonymous and are used interchangeably herein. Fibrous plaque index is defined as the total volume of all voxels corresponding to fibrous tissue within the wall of a vascular segment (e.g. between 65 and 260 HU), divided by the total volume of the respective vascular segment.

Calcium index (Calcium-i) is also known in the art as "(coronary) calcification", "calcium volume" of an artery, and these synonyms may be used interchangeably herein. Calcium-index is defined as the total of volume of all voxels corresponding to local calcium within the wall of a vascular segment (>465 HU), divided by the total volume of the respective coronary segment.

Epicardial adipose tissue volume (EpAT-vol) refers to the total volume of all voxels (within the pre-specified thresholds of −190 to −30 HU) corresponding to epicardial adipose tissue. Epicardial adipose tissue is defined as any adipose tissue located between the myocardium and the pericardium. Alternatively, EpAT-vol can be indexed for differences in body size, e.g. body surface area.

Epicardial adipose tissue Fat Attenuation Index ($FAI_{EpAT}$) refers to the average attenuation of all voxels corresponding to EpAT (within the pre-specified threshold of −190 to −30 HU).

The terms "patient" and "subject" are used interchangeably herein. These terms can refer to any animal (e.g. mammal), including, but not limited to, humans, non-human primates, canines, felines, rodents and the like. Preferably the patient or subject is a human. The patient may be an individual who has been diagnosed as suffering from a condition associated with vascular inflammation or who is suspected of, or at risk of, suffering from a condition vascular inflammation, in particular vascular inflammation affecting the coronary vessels.

A third aspect of the present invention is directed to a novel method for predicting cardiac events, including cardiac death. The method is based on a novel scoring system that has been developed by the present inventors and is referred to herein as the "OxScore (Oxford integrated coronary CT Score)".

The OxScore is based on the observation that vascular inflammation will increase the aqueous phase of the tissue surrounding the inflamed vessel, and this is identified by combining measurements of the volume of this aqueous phase with a shift of the overall attenuation of the tissues surrounding the vessel. When this approach was combined with information about the structure of the vascular wall and epicardial/visceral obesity, the inventors generated a novel score that has been found to be superior to any other imaging biomarker in predicting all-cause and cardiac mortality. This represents a new risk score that predicts mortality due to any or cardiac-specific causes. The method is based on a combination of computed tomography (CT) biomarkers that track vascular inflammation and vulnerable atherosclerotic plaques through volumetric and qualitative changes of the attenuation (or radiodensity) of vascular and perivascular tissues. OxScore provides a unified score that strongly predicts cardiac events and cardiac mortality, and significantly more strongly than any of these indices in isolation.

Uniquely, the OxScore is the only method where coronary artery disease is evaluated by quantification of changes both in the vessel wall, (the location of coronary artery plaques), and in the surrounding tissue (where changes reflect the inflammatory status and risk of the plaque). No other similar approaches have been described previously, and the method of this aspect of the invention is the first to monitor changes in perivascular tissue attenuation and volumetric characteristics to quantify vascular inflammation and cardiovascular risk.

Accordingly, a third aspect of the invention provides a method for predicting the risk of a patient suffering a cardiovascular event, said method comprising:
(a) using data gathered from a computer tomography (CT) scan along a length of a blood vessel to determine:
  (i) calcium index (Calcium-i); and/or
  (ii) fibrous plaque index (FPi)
and at least one of
  (iii) fat attenuation index of the perivascular adipose tissue ($FAI_{PVAT}$); and/or
  (iv) perivascular water index (PVWi), and
with the possible addition of one or more of the following:
  (v) volumetric perivascular characterisation index (VPCI)
  (vi) total epicardial adipose tissue volume (EpAT-vol);
  (vii) fat attenuation index (FAI) of epicardial adipose tissue ($FAI_{EpAT}$),
(b) comparing each of the values determined in (a) to a pre-determined cut-off value or using the absolute value of each variable in order to generate an output value that indicates the patient's risk of suffering a cardiovascular event.

In one embodiment, $FAI_{PVAT}$ is determined in step (a). In another embodiment PVWi is determined in step (a). In a preferred embodiment, both $FAI_{PVAT}$ and PVWi are determined in step (a) of the method. In a further embodiment $FAI_{EpAT}$ is determined in step (a). In another embodiment, $FAI_{PVAT}$ and $FAI_{EpAT}$ or PVWi and $FAI_{EpAT}$ are determined in step (a). In a further embodiment, all of $FAI_{PVAT}$, PVWi and $FAI_{EpAT}$ are determined in step (a).

The indices $FAI_{PVAT}$, PVWi, VPCI, Calcium-i and FPi, $FAI_{EpAT}$, EpAT-vol are as defined herein above.

Preferably, the data is gathered from a CT scan along a length of the right coronary artery, left anterior descending artery, left circumflex artery, aorta, carotid arteries or femoral arteries.

In a preferred embodiment, the data is gathered from a computerised tomography scan along a 4 cm length, starting 1 cm distally to the origin of the right coronary artery.

In a preferred embodiment, the data is gathered from a computerised tomography scan along a length of the aorta.

Figure 3:
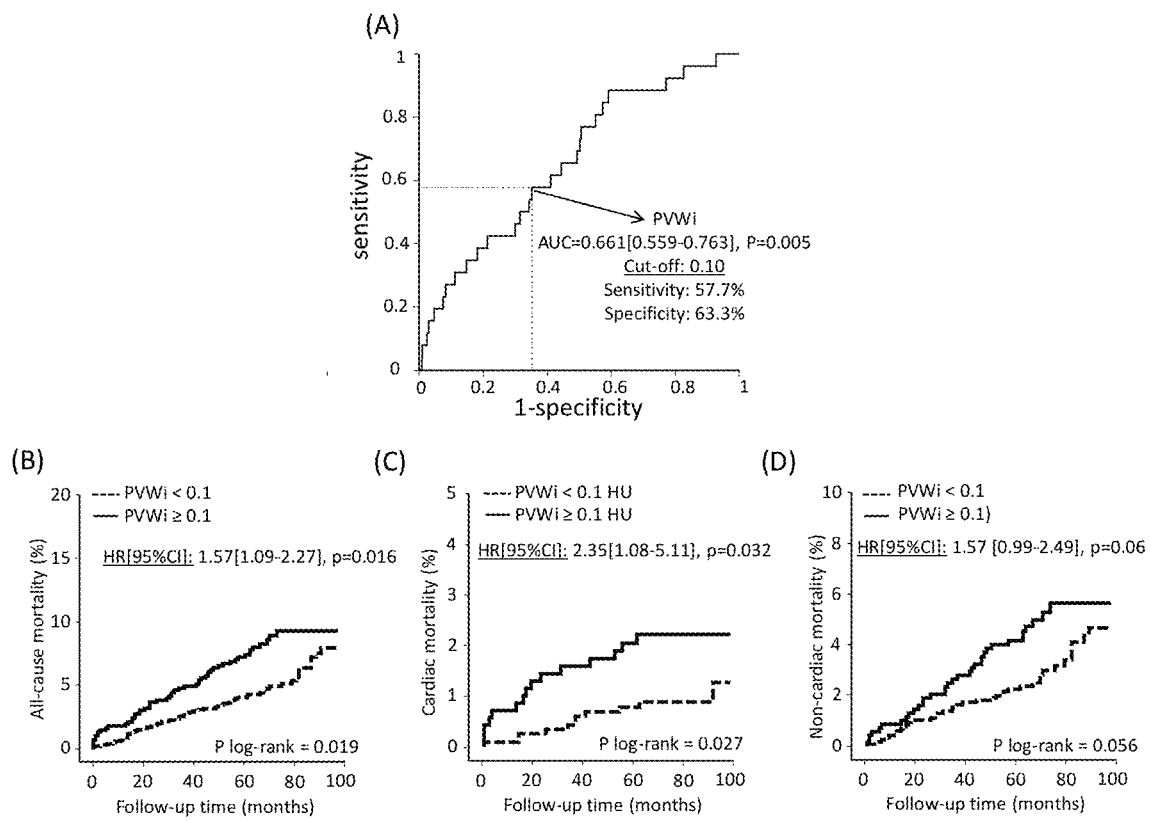
FIG. 3 shows PVWi as a predictor of all-cause, cardiac and non-cardiac mortality. Receiver operating characteristic curve analysis identified a cut-off of 0.10 with 57.7% sensitivity and 63.3% specificity for prediction of cardiac mortality (A). Comparison of KM curves by the log-rank test as well as univariate Cox regression analysis showed that high PVWi values (≥0.10) are associated with a significantly higher risk of all-cause (B) and cardiac mortality (C) but not non-cardiac mortality (p=NS). AUC: area under the curve; CI: confidence intervals; HR: hazard ratio PVWi: Perivascular Water index; ROC: receiver operating characteristic curve.
Figure 4:
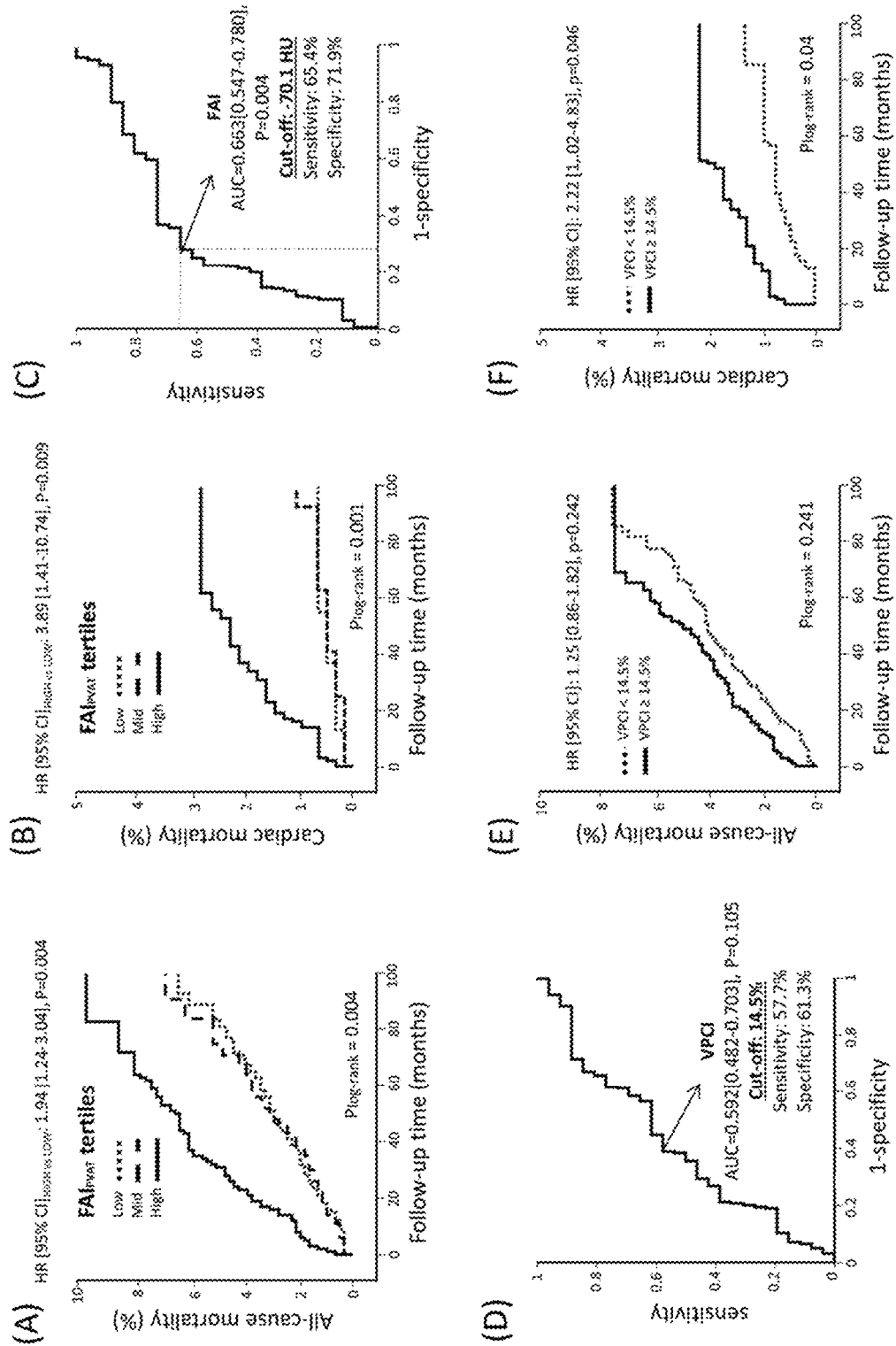
FIG. 4 shows the predictive value of $FAI_{PVAT}$ and VPCI for all-cause and cardiac mortality. We first explored the predictive value of our novel imaging indices by splitting the study population in tertiles according to their respective $FAI_{PVAT}$ and VPCI values. Individuals in the high $FAI_{PVAT}$ group had an almost two-fold increase in their risk of death (A) and almost four times higher risk of cardiac mortality compared to those in the lowest tertile (B). Notably, visual assessment of the Kaplan-Meier curves revealed a similar trend for the mid- and low-tertile groups, suggesting the presence of a certain cut-off, above which the risk of mortality significantly increases. In fact, ROC curve analysis revealed an optimal cut-off of −70.1 HU that was able to predict cardiac death with 65.4% sensitivity and 71.9% specificity (C). By following a similar approach, an optimal cut-off of 14.5% was identified for VPCI as a predictor of cardiac mortality (D). Interestingly, high VPCI values (≥14.5%) were associated with a higher risk of cardiac-related (F) but not all-cause mortality (E). AUC: area under the curve; CI: confidence intervals; $FAI_{PVAT}$: fat attenuation index of perivascular adipose tissue; HR: hazard ratio; ROC: receiver operating characteristic curve, VPCI: volumetric perivascular characterisation index.

Preferably, the cut-off points for each of (i) to (vii) are derived from ROC curves. Based on the ROC curves, an optimal cut-off point is selected that yields the optimal sensitivity and specificity for the prediction of the desired endpoint, e.g. cardiac mortality (see, for example, FIGS. 3, 4).

In one embodiment, the method according to the third aspect of the invention further comprises the age and/or gender of the patient as well as other established cardiovascular risk factors, such as coronary calcium (measured on non-contrast CT scans, e.g. Agatston score), hypertension, hyperlipidemia/hypercholesterolemia, diabetes mellitus, presence of coronary artery disease, smoking, family history of heart disease etc.

In one embodiment, the output value that corresponds to or indicates risk of a cardiac event is a continuous single value function. For example, the absolute values for each variable can be integrated into one single formula along with calculated coefficients to yield an individualised risk prediction/probability.

Figure 9:
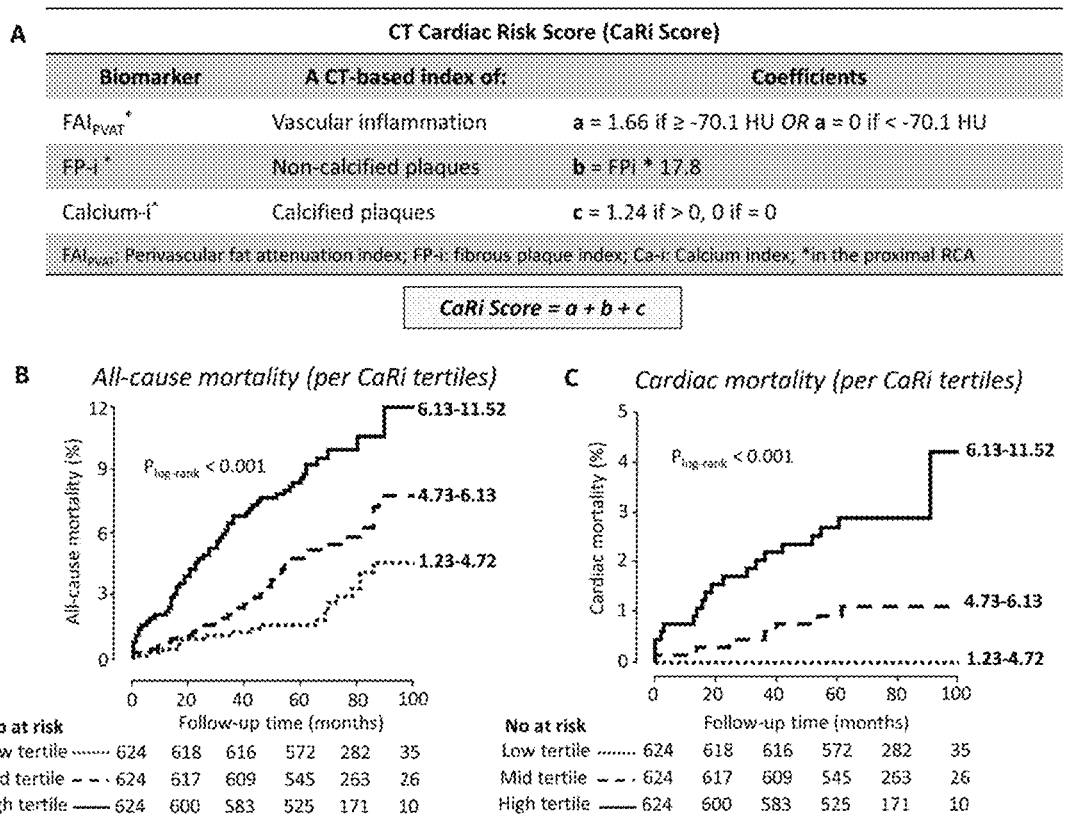
FIG. 9 shows the generation of a novel risk score (Cardiac Risk Score or CaRi Score) by adding the beta coefficients for $FAI_{PVAT}$, FPi and Calcium-i as estimated in an adjusted Cox regression model for cardiac mortality, resulting in a score that ranged from 1.23 to 11.52, with a mean of 5.56 and standard deviation of 1.45 (A). Following multivariable adjustment for age, gender, risk factors and presence of coronary artery disease, CaRi score was identified as a strong and independent predictor of both all-cause and cardiac mortality (adj. HR[95% CI]: 1.46 [1.28-1.65] and 2.71 [1.99-3.69] per 1 unit increments for all-cause and cardiac mortality respectively, P<0.001 for both). Indeed, there was a graded relationship between CaRi score and all-cause/cardiac mortality, with higher CaRi values corresponding to a higher risk of mortality (B, C). (Calcium-i: calcium index; CI: Confidence Interval; $FAI_{PVAT}$: Fat Attenuation Index of Perivascular Adipose Tissue; FPi: fibrous plaque index; HR: hazard ratio; HU: Hounsfield Units).

In an alternative embodiment, the unstandardized beta coefficients of $FAI_{PVAT}$, Calcium-i and FPi, as calculated in a Cox or logistic regression model with cardiac or all-cause mortality as the dependent variable/outcome of interest, can be combined (as shown in FIG. 9) to generate an alternative risk score (e.g. Cardiac Risk score, or CaRi score). An example of the CaRi-based mortality risk score is presented in FIG. 9.

An example for a specific cohort, wherein constants are determined on the basis of the background of the patient cohort, is provided below (also see FIG. 6).

An example of a formula used to calculate the OxScore probability of all-cause/cardiac mortality is provided below.

$$\text{OxScore=Risk (probability) of event (\%)}=100*10^y/(1+10^y)$$

and $\quad y=c+a*FAI_{PVAT}+b*FPi+d*\text{Calcium-I}+e*\text{EpATvol}$ where, a, b, d, e=beta coefficients and c=constant calculated on logistic regression with $FAI_{PVAT}$, FPi, Calcium-I, EpAT volume as the independent variables and all-cause, cardiac mortality or cardiac events as the dependent variable. Alternatively, coefficients can be calculated from Cox regression hazard models.

In one embodiment, both PVWi and $FAI_{PVAT}$ are included in the same model.

In an alternative embodiment, PVWi, $FAI_{PVAT}$, VPCI, FPi, Calcium-i, EpAT volume, $FAI_{EpAT}$, age and gender are all included in the same model. An example of the OxScore-based mortality risk is provided below:

$$\text{OxScore=Risk (probability) of event(\%)}=100*10^y/(1+10^y)$$

where, $y=c+a*FAI_{PVAT}+b*FPi+d*\text{Calcium-I}+e*\text{EpATvol}+f*FAI_{EpAT}+g*\text{PVWi}+h*\text{VPCI}+k*\text{age}+l*\text{gender}$ where, a, b, d, e, f, g, h, k, l=beta coefficients and c=constant calculated on logistic regression with $FAI_{PVAT}$, FPi, Calcium-I, EpAT volume, $FAI_{EpAT}$, PVWi, VPCI, age and gender (as categorical, e.g. 1=male, 0=female) as the independent variables and all-cause, cardiac mortality or cardiac events as the dependent variable. Alternatively, coefficients can be calculated from Cox regression hazard models.

In an alternative embodiment, the output value that corresponds to or indicates risk of a cardiac event is a value that falls within one of three discrete brackets corresponding to low, medium and high risk of suffering a cardiovascular event (see FIG. 6).

Preferably, the patient has been diagnosed with vascular inflammation, or a condition known to be associated with vascular inflammation.

The OxScore and the individual indices on which it is based are useful for predicting cardiac death and cardiac events and so the method of the invention can be used to stratify patients according to their risk of cardiac mortality.

OxScore method can be used as an adjunctive tool in routine clinical CT angiograms to identify patients at high risk of cardiac events and mortality including a sensitive and specific screening tool in people who are apparently healthy and low-risk according to the traditional interpretation of their scans. The OxScore method has utility both in primary prevention (healthy population with no diagnosis of heart disease yet) and secondary prevention (patients with a diagnosis of coronary artery disease), to identify an individual's risk status beyond traditional risk factors, to guide pharmacological treatment decisions, and to monitor response to appropriate medical treatments. To this end, OxScore could be measured automatically using dedicated software providing a rapid, non-invasive estimation of an individual's risk status and guide clinical decision making.

Accordingly, the patient may be an individual who has been diagnosed as suffering from a condition associated with vascular inflammation, or who is suspected of, or at risk of, suffering from a condition vascular inflammation, in particular vascular inflammation affecting the coronary vessels. Alternatively the patient may be a healthy individual who has not been diagnosed as suffering from a condition associated with vascular inflammation, and/or who is not known to be at risk of suffering from a condition vascular inflammation.

Despite the popularity of coronary CT angiography as a diagnostic method for coronary artery disease, coronary calcium score (CCS) remains the only CT-based method of cardiovascular risk stratification, with an established role in clinical practice. However, CCS is only a structural biomarker and only identifies one component of the coronary plaque (calcification), which does not change with the inflammatory status of the vessels and does not improve following appropriate medical management. CCS primarily reflects ageing and it even predicts non-cardiac events (i.e. it is sensitive but not specific for cardiac events). More importantly, no method has been described with an ability to track subclinical changes in coronary inflammation on routine everyday CT angiography.

The OxScore method combines "functional" biomarkers of vascular inflammation (PVWi, VPCI, $FAI_{PVAT}$ and $FAI_{EpAT}$) with indices of structural vascular disease (calcium-i and FPi) and visceral adiposity (EpAT-vol), to generate an integrated scoring system that significantly advances both the diagnostic and prognostic value of routine clinical CT angiography.

Importantly, the method of the invention is non-invasive and is based on the analysis of conventional CT images; it does not require any additional image acquisition.

Certain embodiments of the method of this aspect of the invention can be used for non-invasive monitoring of aortic aneurysms and/or carotid plaques. However, EpAT volume and FAI cannot be applied to other vessels.

The OxScore method may be utilised in a method of treating a condition associated with vascular inflammation in a patient.

According to this aspect of the invention, a method of treating a condition associated with vascular inflammation in a patient comprises carrying out the method according to the third aspect of the invention as described above, and, if the outcome of said method indicates that the patient is at risk of suffering a cardiac event, administering a suitable therapy and/or surgical intervention to said patient.

The invention is further described with reference to the following non-limiting example:

Example

Methods
Patients

In this prospective study, a cohort of 1993 subjects was recruited prospectively between 2005 and 2009, following a clinically indicated CTA performed at the Erlangen University Hospital (Erlangen, Germany). A total of 1872 subjects had analysable CTA scans and were included in the study. The vast majority of the scans were performed for exclusion of coronary artery disease (CAD) (91.7%). Most of the patients had presented with atypical symptoms (85.3%) and less than half had a history of chest pain (43.4%). A minority of the scans (3.8%) was performed in patients with previously known CAD to evaluate possible disease progression (3.7%) or the patency status of a vascular graft (0.1%). Following the baseline CT scan, only a small proportion of the cohort was diagnosed with obstructive CAD (21.6%). The patient demographics and clinical characteristics of the studied population are summarized in Table 1.

TABLE 1

Cohort demographics and clinical characteristics of the study population

| | |
|---|---|
| Subjects screened (n) | 1993 |
| Subjects included in the study (n) | 1872 |
| Age (years) | 60.1 ± 11.9 |
| Male gender (%) | 62.9 |
| Risk factors* | |
| Hypertension (%) | 61.9 |
| Hypercholesterolemia (%) | 54.7 |
| Diabetes Mellitus (%) | 12.4 |
| Active/past smoking (%) | 12.8/21.4 |
| Family history of heart disease (%) | 25.6 |
| Medications at baseline** | |
| Antiplatelets (aspirin/clopidogrel) (%) | 37.6 |
| Statins (%) | 34.6 |
| ACEi or ARBs (%) | 43.1 |
| Beta-blockers (%) | 44.8 |
| CT scan | |
| CT scanner type | |
| 64-slice (%) | 18.1 |
| 64-slice DSCT (%) | 79.2 |
| 128-slice DSCT (%) | 2.7 |
| Tube voltage | |
| 100 keV (%) | 22.2 |
| 120 keV (%) | 77.8 |
| Total Agatston score[†] | |
| <400 (%) | 85.3% |
| ≥400 (%) | 14.7% |
| Follow-up | |
| Duration in months (median [range]) | 72 [51-109] |
| Total mortality n (%) | 114 (6.1) |
| Confirmed cardiac mortality n (%) | 26 (1.4) |
| Confirmed non-cardiac mortality n (%) | 72 (3.8) |
| Unknown cause of death n (%) | 16 (0.9) |

(DS)CT: (dual source) computerised tomography;
values presented as mean ± SD unless otherwise stated;
maximum missingness:
*9.2%,
**13.9%,
[†]24.4%

Study Design

This is a prospective cohort study of subjects who underwent CTA between 2005 and 2009. Follow-up was performed at an average interval of 77.0±14.2 months (range: 51-109 months) after the baseline scan. Data were collected on the primary endpoints of all-cause and cardiac mortality. Significant and independent predictors of all-cause and cardiac-specific mortality were then integrated into a single model, to generate a novel CTA-based method of cardiovascular risk stratification.

Definitions: Cardiac and non-cardiac mortalities were defined according to the "2014 ACC/AHA Key Data Elements and Definitions for Cardiovascular Endpoint Events in Clinical Trials" (Hicks et al., 2015) taking also into account the recommendations of the Academic Research Consortium (Cutlip et al., 2007). Cardiac death was defined as any death due to proximate cardiac causes (e.g. myocardial infarction, low-output heart failure, fatal arrhythmia). Deaths fulfilling the criteria of sudden cardiac death were also included in this group. Any death not covered by the previous definition, such as death caused by malignancy, accident, infection, sepsis, renal failure, suicide or other non-cardiac vascular causes such as stroke or pulmonary embolism was classified as non-cardiac. A subgroup of deaths where the data on the cause of death could not be collected with certainty were classified as "deaths of unknown cause". CAD was defined as the presence of obstructive disease seen on CTA (≥50% stenosis) or previous, known history of CAD.

CT Angiography

All participants underwent coronary CTA and in most of the scans (75.6%) additional non-contrast images were acquired for the purpose of measuring Agatston coronary calcium score. The vast majority of the scans (79.2%) were performed in a dual-source 64-slice scanner, whereas the rest were done either in a 64-slice (18.1%) or dual-source 128-slice scanner (2.7%). Heart rate was optimised using intravenous injection of beta-blockers and sublingual glyceryl-trinitrate (800 ug) was also administered to achieve maximum coronary vasodilatation. CTA was performed following intravenous injection of 95 ml of iodine based contrast medium at a flow rate of 6 mL/sec (tube energy of 80, 100 or 120 kV). Prospective image acquisition was used by ECG-gating at 75% of cardiac cycle (with 100 msec padding for optimal imaging of the right coronary artery if required).

Analysis of CT angiograms: The reconstructed images were transferred to a processing system and analysis workstation (Aquarius Workstation® V.4.4.11 and 4.4.12, TeraRecon Inc., Foster City, CA, USA). Vascular and perivascular tissue components were characterized according to previously described and validated attenuation maps (Obaid et al., 2013). Since our attenuation-based method for characterization of vascular and perivascular tissue has only been validated sufficiently in CT angiograms performed at a tube voltage of either 100 or 120 kV (Obaid et al., 2013; Okayama et al., 2012) scans done at 80 kV (n=14) were excluded from our study. Additional exclusion criteria were the presence of significant artefacts that made the analysis not possible (e.g. blooming or step artefacts) or poor overall image quality that precluded a reliable assessment of the coronary anatomy in the proximal right coronary artery (RCA) or the total epicardial adipose tissue (EpAT). Four researchers blinded to patient demographics and outcomes worked independently for the analysis of the vascular wall perivascular tissue (two researchers) and EpAT (two researchers).

The inter/intra observer variability for these analyses is presented in supplementary Table 2.

TABLE 2

Inter- and intra-observer variability

| Variable | Inter-observer CV (%) | Intra-observer CV (%) |
| --- | --- | --- |
| Vessel diameter | 1.97 | 0.91 |
| Fibrous plaque index | 2.80 | 1.35 |
| Perivascular Water index | 1.78 | 1.68 |
| $FAI_{PVAT}$ | 0.53 | 0.18 |
| EpAT volume | 3.46 | 2.67 |

CV: coefficient of variation;
EpAT: Epicardial Adipose Tissue;
FAI: Fat Attenuation Index;
PVAT: Perivascular Adipose Tissue Agatston coronary calcium score: The Agatston coronary calcium score was calculated on the non-contrast images using standard analysis tools (Aquarius Workstation® V.4.4.11 and 4.4.12, TeraRecon Inc., Foster City, CA, USA).

Adipose tissue analysis: Adipose tissue was defined as all voxels with attenuation within a pre-specified window of −190 to −30 Hounsfield Units (HU). The total EpAT volume was assessed in a semi-automated manner by tracking the contour of the pericardium from the level of the pulmonary artery bifurcation to the apex of the heart at the most caudal end. Voxel attenuation histograms were plotted and FAI was defined as the mean attenuation of all voxels within the pre-specified range of −190 to −30 HU (Tamarappoo et al., 2010; Hell et al., 2016). To adjust for differences in mean attenuation between scans done at different tube voltages, adipose tissue FAI for scans done at 100 kV was divided by a conversion factor of 1.11485 to be comparable to scans performed at 120 kV, as previously described (Okayama, 2012 et al.)

Coronary wall analysis: The vascular segment of interest was identified on 3-dimensional curved multiplanar reconstruction images. For the purposes of our study, analysis was restricted to the proximal 10-50 mm of the RCA. The benefits of this method have been described in our previous work (Antonopoulos et al., in review). In short, the absence of large branches in this segment allows a clear anatomical separation of PVAT and non-perivascular adipose tissue (non-PVAT) compartments, while the proximal 10 mm of the RCA are excluded due to their proximity to the aorta. The lumen as well as the inner and outer wall border were tracked in an automated way with additional manual optimization and validated HU thresholds were applied for characterization of vascular wall components (65 to 260 HU for fibrous plaque and >465 HU for calcification) (Obaid et al., 2013). The Fibrous Plaque index (FPi) and Calcium-index (Calcium-i) were defined by dividing the total volume of fibrous plaque or coronary calcium by the volume of the respective vessel segment.

Perivascular tissue analysis: Following tracking of the segment of interest in the proximal RCA (i.e. the proximal 4 cm of the RCA starting 1 cm away from the RCA ostium), the perivascular area was segmented into 20 concentric cylindrical layers of 1 mm thickness each. Based on our previous work (Antonopoulos et al., in review), we defined PVAT as adipose tissue located within a radial distance equal to the diameter of the respective vessel extending from the outer vessel wall. This is based on a biological definition of PVAT derived from adipose tissue biopsies from the perivascular area which demonstrated a different adipose tissue phenotype (with smaller adipocytes, lower expression of adipogenic genes and less lipophilic/greater aqueous phase) close to the vessel compared with adipose tissue 2 cm away from the vascular wall. In addition, mean attenuation of PVAT has been shown to be independent of lumen attenuation (Antonopoulos et al., in review), thus avoiding a partial volume effect (Hell et al., 2016) Voxel attenuation histograms were plotted and the mean attenuation of all voxels characterized as adipose tissue within this volume was defined as $FAI_{PVAT}$. Next, the respective FAI index was calculated for adipose tissue in each of the 20 concentric cylindrical layers and was plotted against the radial distance from the outer vessel wall. On the other hand, $FAI_{non-PVAT}$ was defined as the FAI value of adipose tissue in the most distal cylindrical layer (2 cm away from the vascular wall). In order to describe the change in adipose tissue attenuation between PVAT and non-PVAT, the volumetric perivascular characterization index (VPCI) was created and was defined as the % change from $FAI_{PVAT}$ to $FAI_{non-PVAT}$ [VPCI=100× $(FAI_{PVAT}-FAI_{non-PVAT})/|FAI_{PVAT}|$] (FIG. 1). In our previous work (Antonopoulos et al, under review) we found that VPCI correlates with the presence of "soft atherosclerotic plaques", as defined by using the standard plaque analysis methodology (Obaid et al., 2013).

Based on our working hypothesis that vascular inflammation impairs the differentiation of adipocytes and shifts the balance towards a greater aqueous than lipophilic phase, we then tracked the volume of the aqueous phase in the perivascular area by applying an attenuation window of −15 to +15 HU. The total volume of all voxels within this range was then divided by the total perivascular volume to define the Perivascular Water Index (PVWi).

Statistical Analysis

All continuous variables were tested for normal distribution using the Kolmogorov-Smirnov test. Mean values between two independent groups were compared by unpaired Student's t-test or Mann-whitney U test as appropriate, while one-way ANOVA or Kruskal-Wallis test was used for comparisons between three or more groups. Correlations between continuous variables were assessed with Pearson's r or Spearman's rho coefficient, as appropriate.

The predictive value of the variables of interest for the primary endpoints of all-cause and cardiac mortality was first tested in univariate Cox regression analysis, and Kaplan-Meier curves were generated and compared by the log-rank test. Based on receiver operating curve (ROC) analysis, an appropriate cut-off was identified for PVWi, $FAI_{PVAT}$ and VPCI and the imaging biomarkers were then tested in a multivariable Cox regression model, adjusting for age, gender, traditional risk factors, clinically relevant medication, image acquisition parameters, presence of CAD and Agatston score. Imaging biomarkers derived from a standard coronary CTA that were found to be independent predictors of all-cause/cardiac mortality were selected to generate a novel predictive model for cardiovascular risk stratification. Based on bivariate logistic regression, an individual probability (risk) was calculated for each study participant and the study population was stratified according to the respective risk for all-cause or cardiac mortality. Then the additional predictive value of our set of biomarkers ("OxScore") was compared against a standard model composed of age, gender, cardiovascular risk factors, CAD and Agatston score ($\geq 400$ vs <400) (Model 1). The predictive value of Model 1 was compared against Model 2 (Model 1+OxScore variables) by the Wald Chi-square test and the C-statistic (Area Under the Curve) of the respective receiver operating characteristic (ROC) curves both for cardiac and all-cause mortality. Risk restratification of the study population was quantified by the Net Reclassification Improvement index.

Results

Patients and Outcomes

Among the 1993 subjects who underwent CTA, 121 scans were excluded (107 due to poor image quality or presence of artefacts, 14 scans performed at 80 kV), leaving 1872 suitable for analysis. The subjects were followed up for an average of 77±14.2 months after the baseline scan [range from 51 to 109 months]. During the follow up, there were 114 deaths (26 confirmed cardiac (1.4%), 72 confirmed non-cardiac (3.8%) and 16 deaths of unknown cause (0.9%)).

Validation of the Method

Figure 2:
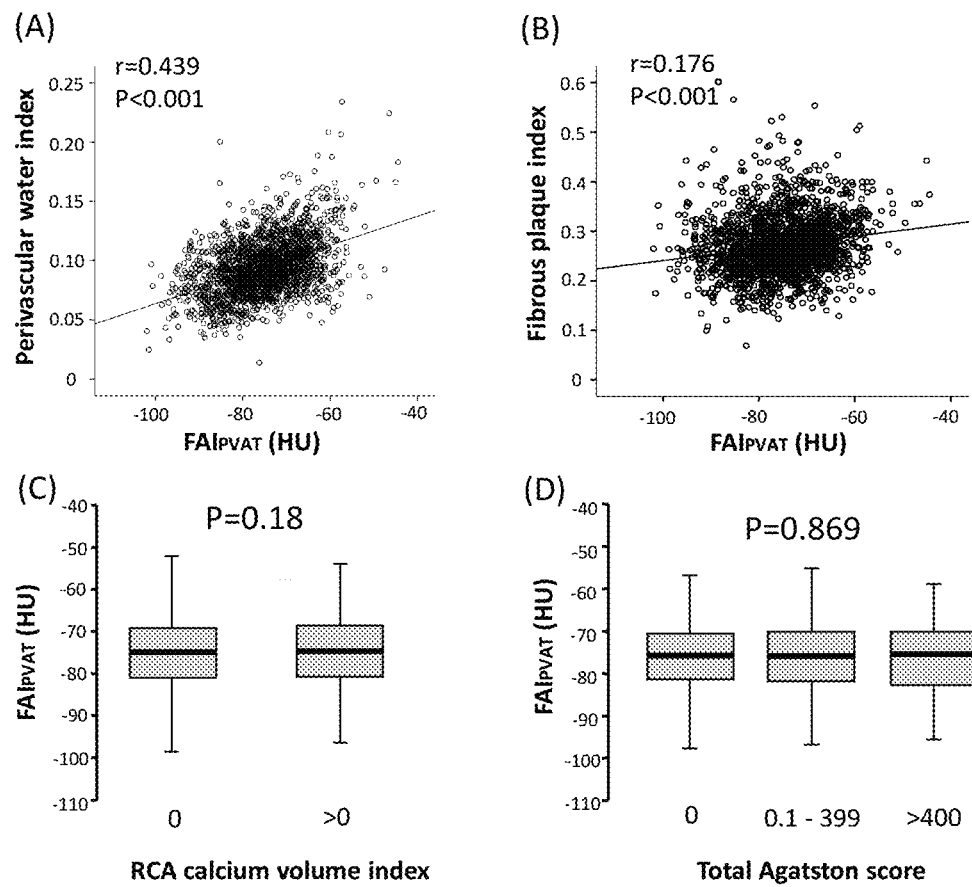
FIG. 2 shows the correlation between perivascular fat attenuation index ($FAI_{PVAT}$), perivascular water index (PVWi), fibrous plaque index (FPi) and coronary calcification. $FAI_{PVAT}$ is strongly correlated with perivascular water, supporting the hypothesis that changes in $FAI_{PVAT}$ reflect a shift from a lipophilic to a greater aqueous phase (A). On the other hand, there was only a weak correlation between $FAI_{PVAT}$, a functional biomarker, and FPi, a structural wall biomarker, suggesting that the two indices reflect a different local biology (B). Similarly, no correlation was found between $FAI_{PVAT}$ and coronary calcium (RCA calcium index and total Agatston score) (C, D). Taken together, these findings suggest that $FAI_{PVAT}$ describes a different biology than anatomical plaque burden and it is entirely independent of the local calcium load or the Agatston score.

In accordance with our previous findings, in this study we observed a strong correlation between $FAI_{PVAT}$ and PVWi (FIG. 2A). $FAI_{PVAT}$ was only weakly correlated with FPi (r=0.179, P<0.001, FIG. 2B) but there was no significant correlation between $FAI_{PVAT}$ and either RCA calcium-i (P=0.18, FIG. 2C) or total Agatston score (P=0.869, FIG. 2D). These findings confirmed that $FAI_{PVAT}$ describes a different (although indirectly related) biology, distinct from anatomical plaque burden and is entirely independent of the presence of coronary artery calcification. However, since PVWi and $FAI_{PVAT}$ describe a similar biology they were not included in the same multivariable model.

Prediction of Mortality

The predictive value of PVWi was first tested in ROC analysis that identified a cut-off of 0.10 with 57.7% sensitivity and 63.3% specificity for prediction of cardiac mortality (FIG. 3A). Comparison of KM curves by the log-rank test as well as univariate Cox regression analysis showed that high PVWi values ($\geq 0.10$) are associated with a significantly higher risk of all-cause (FIG. 3B) and cardiac mortality (FIG. 3C) but not non-cardiac mortality (p=NS, FIG. 3D).

Next, the predictive value of $FAI_{PVAT}$ and VPCI were tested in univariate Cox regression hazard models. Individuals in the highest tertile of $FAI_{PVAT}$ had a significantly higher risk of both all-cause and cardiac mortality, compared to those in the low tertile (FIG. 4A-B). In ROC curve analysis for cardiac mortality, a cut-off of −70.1 HU was identified as the value yielding the optimal sensitivity and specificity for $FAI_{PVAT}$ as a predictor of cardiac death (65.4% and 71.9% respectively) (FIG. 4C). By following a similar approach, an optimal cut-off of 14.5% was identified for VPCI as a predictor of cardiac mortality (FIG. 4D). Interestingly, high VPCI values ($\geq 14.5\%$) were associated with a higher risk of cardiac-related but not all-cause mortality (FIG. 4E-F).

In univariate Cox-regression analysis (Table 3), both high $FAI_{PVAT}$ values ($\geq -70.1$ HU) and $FAI_{EpAT}$ were found to be significant predictors of all-cause and cardiac mortality but not non-cardiac death, with higher adipose tissue attenuation in both depots linked to a higher all-cause or cardiac-specific mortality risk (FIG. 5A-B). High VPCI values ($\geq 14.5\%$) were also associated with a two-fold increase in the risk of cardiac death, but not all-cause or non-cardiac mortality. Fibrous plaque burden (measured by FPi) was a significant predictor of all-cause and cardiac deaths, but not non-cardiac mortality. Epicardial obesity (measured by EpAT-vol) and coronary calcification (Calcium-$i_{RCA}$) were also found to be significant predictors of all three endpoints.

TABLE 3

Univariate Cox regression for prediction of all-cause, cardiac and non-cardiac mortality

| CTA-derived indices | All-cause mortality HR[95% CI], p value | Cardiac mortality HR[95% CI], p value | Non-cardiac mortality HR[95% CI], p value |
| --- | --- | --- | --- |
| PVWi ($\geq 0.1$ versus <0.1) | 1.57 [1.09-2.27], p = 0.016 | 2.35 [1.08-5.11], p = 0.032 | 1.57 [0.99-2.49], p = 0.06 |
| $FAI_{PVAT}$ ($\geq -70.1$ HU vs <−70.1 HU) | 2.11 [1.445-3.082], p < 0.001 | 5.206 [2.298-11.975], p < 0.001 | 1.516 [0.923-2.491], p = 0.100 |
| $FAI_{EpaT}$ (per 1 HU increase) | 1.043 [1.012-1.075], p = 0.006 | 1.081 [1.016-1.152], p = 0.014 | 1.035 [0.996-1.075], p = 0.08 |

TABLE 3-continued

Univariate Cox regression for prediction of all-cause, cardiac and non-cardiac mortality

| CTA-derived indices | All-cause mortality HR[95% CI], p value | Cardiac mortality HR[95% CI], p value | Non-cardiac mortality HR[95% CI], p value |
|---|---|---|---|
| Calcium-i (>0 vs 0) | 3.606 [2.493-5.217], p < 0.001 | 5.644 [2.59-12.3], p < 0.001 | 3.093 [1.934-4.945], p < 0.001 |
| FPi (per 0.01 unit increase) | 1.037 [1.007-1.067], p = 0.014 | 1.115 [1.064-1.17], p < 0.001 | 1.011 [0.973-1.051], p = 0.56 |
| EpAT volume (per $cm^3$ increase) | 1.006 [1.003-1.009], p < 0.001 | 1.007 [1.001-1.012], p = 0.021 | 1.005 [1.001-1.009], p = 0.008 |
| VPCI (≥14.5% vs <14.5%) | 1.250 [0.860-1.817], p = 0.242 | 2.215 [1.015-4.832], p = 0.046 | 1.037 [0.642-1.676], p = 0.881 |
| Agatston CCS (≥400 vs <400) | 3.457 [1.635-3.861], p < 0.001 | 3.08 [0.927-10.235], p = 0.066 | 3.339 [1.854-6.015], p < 0.001 |

EpAT: Epicardial Adipose Tissue;
CCS: Agatston coronary calcium score,
CI: Confidence interval,
FAI: Fat Attenuation Index,
FPi: Fibrous Plaque index;
HR: Hazard Ratio,
HU: Hounsfield units,
PVAT: Perivascular Adipose Tissue,
PVWi: perivascular water index;
VPCI: Volumetric Perivascular Characterisation Index Survival analysis of the 16 deaths of unknown cause, identified coronary calcification and EpAT volume as significant predictors of mortality (HR [95%]: 3.45 [1.28-9.28], p=0.014 for calcium-i, 4.24 [1.51-11.93], p=0.006 for Agatston score and 1.008 [1.001-1.015], p=0.018 for EpAT volume (in $cm^3$). There was a non-significant trend for higher mortality with high $FAI_{PVAT}$ values (HR [95% CI]: 1.98 [0.70-5.57], p=0.198). No significant predictive value was found for VPCI (HR [95% CI]: 1.10 [0.40-3.04], p=0.861), FPi (HR [95%]: 0.99 [0.91-1.07], p=0.74) or $FAI_{EpAT}$ (HR [95% CI]: 1.02 [0.94-1.11], P=0.63) as predictors of the deaths of unknown cause.

Multivariable adjustment for age, gender, traditional risk factors, presence of CAD, clinically relevant medication at baseline, CT scanner type and Agatston score (≥400 vs<400) identified $FAI_{PVAT}$ as a strong independent predictor of all-cause mortality, driven mainly by cardiac but not non-cardiac mortality (Table 3, FIG. 5C). Indeed, $FAI_{PVAT}$≥−70.1 HU was linked to an almost two-fold increase in the adjusted risk for all-cause and to a more than five-fold increase in the risk for cardiac mortality over an average of 6.4 years, compared to individuals in the low $FAI_{PVAT}$ group. Notably, these effects were independent of the average radiodensity or total volume of the EpAT depot. EpAT volume, a marker of epicardial adiposity, was a significant predictor of mortality, while fibrous plaque burden and vascular calcification (measured as FPi and calcium-i in the proximal RCA respectively) were also identified as strong and independent predictors of all-cause mortality.

TABLE 4

Multivariable Cox regression for prediction of all-cause, cardiac and non-cardiac mortality

| CTA-derived indices | All-cause mortality HR[95% CI], P value | Cardiac mortality HR[95% CI], P value | Non-cardiac mortality HR[95% CI], P value |
|---|---|---|---|
| $FAI_{PVAT}$ (≥70.1 HU vs <−70.1 HU) | 1.786 [1.058-3.014], p = 0.03 | 5.433 [1.642-17.976], p = 0.006 | 1.232 [0.631-2.407], p = 0.541 |
| $FAI_{EpAT}$ (per 1 HU increase) | 1.048 [1.00-1.100], p = 0.052 | 1.001 [0.904-1.107], p = 0.991 | 1.059 [0.997-1.125], p = 0.064 |
| Calcium-i (>0 vs 0) | 1.882 [1.179-3.005], p = 0.008 | 3.351 [1.241-9.044], p = 0.017 | 1.593 [0.867-2.927], p = 0.133 |
| FPi (per 0.01 unit increase) | 1.054 [1.021-1.088], p = 0.001 | 1.174 [1.092-1.263], p < 0.001 | 1.027 [0.986-1.070], p = 0.198 |
| EpAT volume (per 1 $cm^3$ increase) | 1.008 [1.004-1.012], p < 0.001 | 1.008 [0.998-1.018], p = 0.137 | 1.007 [1.001-1.013], p = 0.022 |
| VPCI (≥14.5% vs <14.5%) | 0.780 [0.512-1.188], p = 0.247 | 1.000 [0.386-2.588], p = 0.999 | 0.739 [0.432-1.262], p = 0.268 |
| Agatston CCS (≥400 vs <400) | 1.267 [0.717-2.240], p = 0.416 | 0.598 [0.172-2.077], p = 0.419 | 1.512 [0.727-3.142], p = 0.268 |

Model adjusted for: age, gender, hypertension, hypercholesterolemia, diabetes mellitus, active smoker status, medications at baseline (antiplatelets, statins), presence of coronary artery disease, CT scanner used, Agatston CCS score (≥400 vs<400); CTA: Computed tomography angiography; CCS: coronary calcium score, CI: Confidence interval, FAI: fat attenuation index, HR: hazard ratio, CI: Confidence interval; HU: Hounsfield units, PVAT: perivascular adipose tissue; EpAT: Epicardial adipose tissue; FPi: Fibrous plaque index; VPCI: Volumetric perivascular characterization index.

The OxScore

Next, all four imaging biomarkers that were found to be independent predictors of mortality were combined to generate a novel cardiac CTA risk score that would be easy to calculate in routine clinical CTA, the "OxScore" (FIG. 3A). The four biomarkers that were included in the model (namely $FAI_{PVAT}$, FPi, Calcium-I and EpAT-vol) describe different aspects of cardiac and coronary physiology and can be calculated using semi-automated techniques on routine contrast CTA images. $FAI_{PVAT}$ is a novel marker of vascular inflammation, while FPi and calcium-i reflect local structural disease by describing the presence of fibrous or calcified/mixed plaques. Finally, EpAT-volume is a marker of epicardial adiposity, a well-established risk factor of adverse cardiometabolic events.

Combination of these four indices into a combined model (OxScore) generated an individualised risk score for all-cause and cardiac-specific death (FIG. 6). Stratification of the study population based on the proposed model identified a high-risk subgroup ($OxScore_{high}$) with an almost eight-fold higher risk of all-cause mortality compared to the low-risk group ($OxScore_{low}$). Similarly, application of the novel model identified a group of 192 study participants with a significantly higher risk of cardiac death during follow-up compared to the low-risk subgroup of 1680 study participants (FIG. 6B-E).

Comparison of the OxScore Against Traditional Cardiac CT Indices

Next, the predictive value of the new OxScore model was compared against traditional risk factors and cardiac CT indices, including the presence of high coronary calcium (as demonstrated by an Agatston score of ≥400 versus <400) and obstructive CAD. Two predictive models were constructed as follows: Model 1: age, gender, hypertension, hypercholesterolemia, diabetes mellitus, current smoker status, CAD and Agatston score (≥400 versus <400), Model 2: Model 1+OxScore variables ($FAI_{PVAT}$, FPi, Calcium-I, EpAT volume). Both models were significant predictors of all-cause and cardiac mortality, as demonstrated in ROC curve analysis (FIG. 7A, C). However, addition of the OxScore into the standard model significantly improved the predictive power of the overall model (A[AUC]=0.031, P<0.05) with respect to all-cause mortality (FIG. 7A) and resulted in a net reclassification of 7.6% of the study population (NRI=7.6%), mainly by improving classification of non-events (FIG. 7B). By following a similar approach for cardiac mortality, inclusion of OxScore resulted in an even more pronounced, significant improvement in the predictive value of the model (Δ[AUC]=0.10, P<0.01) while also improving cardiac risk classification (NRI=11.3%).

Validation of Perivascular Indices in Other Vessels

Figure 8:
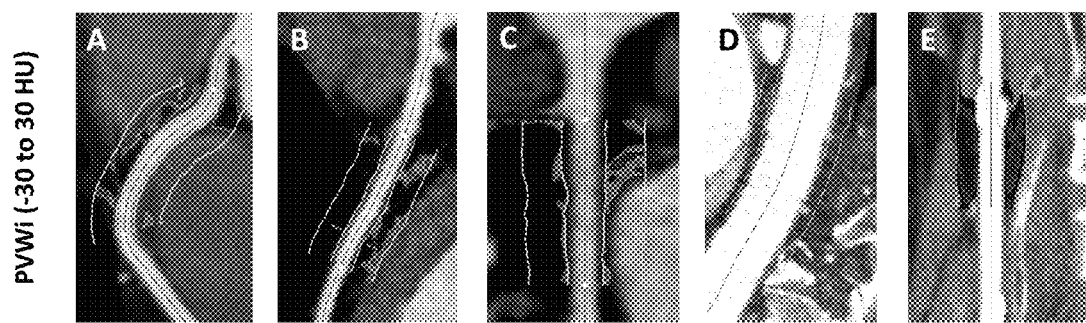
FIG. 8 shows how PVWi (perivascular water index) is calculated around different vessels. PVWi is calculated along the right coronary artery (RCA) (A), left anterior descending artery (LAD) (B), left circumflex artery (LCx) (C), aorta (D) and the common carotid artery (E), respectively.

Finally, we explored whether perivascular indices such as perivascular water index, can be measured along vessels other than the proximal RCA. FIG. 8 demonstrates how PVWi is calculated around different vessels. More specifically, PVWi is calculated along the right coronary artery (RCA) (FIG. 8A), left anterior descending artery (LAD) (FIG. 8B), left circumflex artery (LCx) (FIG. 8C), aorta (FIG. 8D) and the common carotid artery (FIG. 8E), respectively.

Discussion

In this study the present inventors demonstrate that a novel imaging biomarker, that detects coronary artery inflammation by analysing the spatial changes of CT attenuation of peri-coronary adipose tissue ($FAI_{PVAT}$), is a powerful predictor of all-cause and cardiac mortality. As a previously validated biomarker of vascular inflammation, the new index advances significantly the current state of the art, by overcoming the limitations of calcium or fibrous plaque indices, that are driven by non-reversible structural changes of the vascular wall. By combining $FAI_{PVAT}$ with a number of structural biomarkers, derived from the same segment of the coronary artery (Calcium-I, FPi) as well as total EpAT volume, the inventors have created a new integrated CTA risk score, the OxScore, that enables re-stratification of subjects in both primary and secondary prevention based on routine CTA, dissociating risk prediction from the simple presence of atherosclerotic plaques or calcification. This new re-stratification can be applied both prospectively and retrospectively in routine CTA imaging, and may guide the targeted deployment of more aggressive preventive strategies to a significant proportion of subjects where CTA does not reveal significant anatomical coronary artery disease, but the risk of future coronary events remains high.

Early, non-invasive diagnosis of vascular inflammation (an early biological process preceding plaque formation but also leading to plaque rupture) has been hailed as the "holy grail" of CAD diagnostics and could help improve risk stratification in primary and secondary prevention. However, the current state-of-the-art methods for the diagnosis of vascular inflammation and cardiovascular risk prediction are suboptimal and have several limitations. Circulating inflammatory biomarkers (e.g. CRP, TNF-α) have a limited value in cardiovascular risk prediction since they are not specific to the cardiovascular system and have poor correlation with local vascular inflammation (Weintraub et al., 2000; Lee et al., 2012; Margaritis et al., 2013). In the field of cardiovascular imaging, the predictive value of Agatston coronary calcium score measured by CT has been long-established (Greenland et al., 2004). However, coronary calcification represents a non-reversible process that does not change in response to appropriate medical therapy (e.g. statins) (Alexopoulos et al., 2013). In fact, calcified plaques are considered more stable and less likely to rupture compared to plaques with high-risk features, such as a thin-cap fibroatheromas and a large necrotic core (Huang et al., 2001). Detection of high-risk plaque features such as microcalcification, a large necrotic core or positive remodelling on CTA have all been shown to predict future cardiac events (Hecht et al., 2015; Saremi et al., 2015) but the reliability of the method is affected by the observer's expertise and CT settings and parameters, including spatial resolution (Maurovich-Horvat et al., 2014; Maurovich-Horvat et al., 2014; Fleg et al., 2012). Newer invasive methods such as optical coherence tomography (OCT) and intravascular ultrasound (IVUS) have been more successful in detecting high-risk plaques but are invasive, expensive, carry a small yet significant risk of in-procedure complications (Bezerra et al., 2009; McDaniel et al., 2011) and are not suitable for primary prevention and wide screening of low-risk individuals. Positron emission tomography (PET) with $^{18}F$-FDG is expensive, associated with significantly higher levels of radiation exposure compared to CT alone, not readily available and limited by myocardial uptake of the radiotracer that results in significant background noise (Rogers et al., 2011; Joshi et al., 2014). Even the introduction of newer radiotracers (such as $^{18}$F—NaF), although promising, carries many of the limitations of traditional PET imaging, including but not limited to significant radiation exposure, limited availability and no demonstrated value in primary or even secondary prevention (Joshi et al., 2014). Therefore, there is still need for a functional biomarker that will describe vascular inflammation rather than structural and non-reversible changes in the vascular wall. This biomarker should be easy to obtain through routine tests that are already performed under the current clinical guidelines.

In their previous work, the present inventors have demonstrated that $FAI_{PVAT}$ is positively associated with the presence of CAD and the volume of fibrous plaque in the proximal RCA independently of the presence of coronary calcium. In the same study, it was shown that $FAI_{PVAT}$ changes in a dynamic way in response to local rupture of a culprit lesion in patients with acute MI and can distinguish culprit from non-culprit lesions. These observations supported the inventors' hypothesis that $FAI_{PVAT}$ could function as a dynamic biomarker of vascular inflammation and cardiovascular risk and offer diagnostic and prognostic information beyond that of traditional biomarkers, such as coronary calcium.

In the current study the present inventors explore the predictive value of $FAI_{PVAT}$ along with other vascular/perivascular imaging biomarkers in a large prospective cohort of mid-low risk individuals undergoing coronary CTA and a mean follow-up of 6.4 years. High $FAI_{PVAT}$ was found to be a significant and independent predictor of all-cause and cardiac but not non-cardiac mortality, independently of age, gender, traditional cardiovascular risk factors, presence of CAD and coronary calcium. The predictive value of $FAI_{PVAT}$ appears to be driven by cardiac rather than non-cardiac mortality. This is in accordance with the underlying biology, given that $FAI_{PVAT}$ is believed to be affected by local rather than systemic inflammation.

More importantly, this study is the first to describe the predictive value of peri-coronary adipose tissue quality characterized by non-invasive CTA. Previous studies have described that lower attenuation of the visceral and subcutaneous adipose tissue depots on CT is associated with adverse cardiometabolic effects independently of fat volume (Rosenquist et al., 2013) while decreasing attenuation in the same depots has more recently been associated with a deterioration of traditional cardiovascular risk factors (Lee et al., 2016). Similarly, lower attenuation in the EpAT has been associated with high-risk plaque features (Lu et al., 2016). In this regard, the findings of the present inventors are radical, since they demonstrate an opposite, "paradoxical" trend for PVAT attenuation. However, these observations are in line with previous studies of the present inventors on the interplay between the vascular wall and PVAT and the effects of vascular inflammation on PVAT quality. Taken together, these findings suggest that local rather than systemic factors affect PVAT quality, and contrary to other fat depots, PVAT quality can function as a "sensor" of inflammation in the underlying coronary artery and therefore a specific predictor of adverse cardiac events.

It is evident that $FAI_{PVAT}$ describes a different vascular biology than FPi and Calcium-i. While the latter two biomarkers reflect structural changes of the vascular wall (namely fibrous plaque and vascular calcification respectively), $FAI_{PVAT}$ is a dynamic marker of vascular inflammation. Indeed, using multivariable cox regression models, we demonstrated that $FAI_{PVAT}$ is a strong predictor of all-cause and cardiac mortality independently of FPi and calcium-i, even after adjustment for potential confounders, such as age, gender, epicardial fat volume, cardiovascular risk factors and clinically relevant medication. On the contrary, the predictive value of calcium-i or Agatston score (current CTA biomarker recommended for risk stratification) is significantly reduced or eliminated in multivariable models after adjustment for age, suggesting that vascular calcification, is at least partly, a surrogate of ageing.

As previously discussed, current scoring systems for cardiovascular risk prediction often fail to detect "vulnerable subjects" for cardiac events within populations of mid-low risk asymptomatic individuals. More than half of ruptured plaques derive from lesions that were previously asymptomatic and non-obstructive (<50% stenosis) (Fishbein et al., 1996). Similar lesions are frequently seen on CT angiograms but there is currently no available method to identify which patients are at high-risk and therefore in need of more aggressive medical intervention. A quick, reliable, easy-to-use and readily available method that would detect this group of patients would be invaluable in the clinical setting. In the current study, the present authors combined our observations on the predictive value of $FAI_{PVAT}$ along with other indices of the perivascular and vascular tissue into a novel score, the OxScore. The proposed scoring method takes into account traditional structural biomarkers of vascular disease (Calcium-i, FPi), adiposity (EpAT volume) and combines them with a novel functional index of coronary and perivascular tissue inflammation ($FAI_{PVAT}$) to generate a powerful tool for cardiovascular risk stratification. Overall, OxScore was not only an independent predictor of future mortality, but more importantly improved risk stratification beyond the traditional interpretation of a CTA scan, that includes Agatston score and/or the presence of obstructive CAD.

CONCLUSIONS

The present inventors have demonstrated a new imaging biomarker for detection of coronary artery inflammation, through quantification of CT attenuation of peri-coronary adipose tissue. The new biomarker, Perivascular Fat Attenuation Index ($FAI_{PVAT}$), predicts all-cause and cardiac mortality independently of traditional risk factors, the presence of CAD and coronary calcification. The present inventors now propose a novel CT-based risk score, the OxScore, that significantly improves cardiac risk stratification of low to mid-risk individuals undergoing routine CTA. Based on the current findings and its simplicity, the method can even be applied retrospectively in existing scans and re-stratify populations who have been discharged following CT angiograms with non-obstructive disease. This method has the potential to change clinical practice, establishing coronary CTA as a powerful prognostic tool in both primary and secondary prevention.

REFERENCES

Alexopoulos, N., et al. (2013). "Effect of intensive versus moderate lipid-lowering therapy on epicardial adipose tissue in hyperlipidemic post-menopausal women: a substudy of the BELLES trial (Beyond Endorsed Lipid Lowering with EBT Scanning)." *J Am Coll Cardiol* 61(19): 1956-1961.

Bezerra, H. G., et al. (2009). "Intracoronary optical coherence tomography: a comprehensive review clinical and research applications." *JACC Cardiovasc Interv* 2(11): 1035-1046.

Cutlip, D. E., et al. (2007). "Clinical end points in coronary stent trials: a case for standardized definitions." *Circulation* 115(17): 2344-2351.

Fishbein, M. C. and R. J. Siegel (1996). "How Big Are Coronary Atherosclerotic Plaques That Rupture?" *Circulation* 94(10): 2662-2666.

Fleg, J. L., et al. (2012). "Detection of high-risk atherosclerotic plaque: report of the NHLBI Working Group on current status and future directions." *JACC Cardiovasc Imaging* 5(9): 941-955.

Greenland, P., et al. (2004). "Coronary artery calcium score combined with Framingham score for risk prediction in asymptomatic individuals." *JAMA* 291(2): 210-215.

Hecht, H. S., et al. (2015). "High-Risk Plaque Features on Coronary CT Angiography." *JACC Cardiovasc Imaging* 8(11): 1336-1339.

Hell, M. M., et al. (2016). "CT-based analysis of pericoronary adipose tissue density: Relation to cardiovascular risk factors and epicardial adipose tissue volume." *J Cardiovasc Comput Tomogr* 10(1): 52-60.

Hicks, K. A., et al. (2015). "2014 ACC/AHA Key Data Elements and Definitions for Cardiovascular Endpoint Events in Clinical Trials: A Report of the American College of Cardiology/American Heart Association Task Force on Clinical Data Standards (Writing Committee to Develop Cardiovascular Endpoints Data Standards)." *J Am Coll Cardiol* 66(4): 403-469.

Huang, H., et al. (2001). "The impact of calcification on the biomechanical stability of atherosclerotic plaques." *Circulation* 103(8): 1051-1056.

Joshi, N. V., et al. (2014). "18F-fluoride positron emission tomography for identification of ruptured and high-risk coronary atherosclerotic plaques: a prospective clinical trial." *Lancet* 383(9918): 705-713.

Lee, J. J., et al. (2016). "Association of Changes in Abdominal Fat Quantity and Quality With Incident Cardiovascular Disease Risk Factors." *J Am Coll Cardiol* 68(14): 1509-1521.

Lee, R., et al. (2012). "Evaluating oxidative stress in human cardiovascular disease: methodological aspects and considerations." *Curr Med Chem* 19(16): 2504-2520.

Lu, M. T., et al. (2016). "Epicardial and paracardial adipose tissue volume and attenuation—Association with high-risk coronary plaque on computed tomographic angiography in the ROMICAT II trial." *Atherosclerosis* 251: 47-54.

Margaritis, M., et al. (2013). "Interactions between vascular wall and perivascular adipose tissue reveal novel roles for adiponectin in the regulation of endothelial nitric oxide synthase function in human vessels." *Circulation* 127(22): 2209-2221.

Maurovich-Horvat, P., et al. (2014). "Comprehensive plaque assessment by coronary CT angiography." *Nat Rev Cardiol* 11(7): 390-402.

McDaniel, M. C., et al. (2011). "Contemporary clinical applications of coronary intravascular ultrasound." *JACC Cardiovasc Interv* 4(11): 1155-1167.

Obaid, D. R., et al. (2013). "Atherosclerotic plaque composition and classification identified by coronary computed tomography: assessment of computed tomography-generated plaque maps compared with virtual histology intravascular ultrasound and histology." *Circ Cardiovasc Imaging* 6(5): 655-664.

Okayama, S., et al. (2012). "The influence of effective energy on computed tomography number depends on tissue characteristics in monoenergetic cardiac imaging." *Radiol Res Pract* 2012: 150980.

Rogers, I. S. and A. Tawakol (2011). "Imaging of coronary inflammation with FDG-PET: feasibility and clinical hurdles." *Curr Cardiol Rep* 13(2): 138-144.

Rosenquist, K. J., et al. (2013). "Visceral and subcutaneous fat quality and cardiometabolic risk." *JACC Cardiovasc Imaging* 6(7): 762-771.

Saremi, F. and S. Achenbach (2015). "Coronary plaque characterization using CT." *AJR Am J Roentgenol* 204(3): W249-260.

Tamarappoo, B., et al. (2010). "Increased pericardial fat volume measured from noncontrast CT predicts myocardial ischemia by SPECT." *JACC Cardiovasc Imaging* 3(11): 1104-1112.

Weintraub, W. S. and D. G. Harrison (2000). "C-reactive protein, inflammation and atherosclerosis: do we really understand it yet?" *Eur Heart J* 21(12): 958-960.

The invention claimed is:

1. A method of predicting a mortality risk or risk of a patient suffering a cardiovascular event, said method comprising:
   (a) determining:
      (i) epicardial adipose tissue volume (EpAT-vol); and at least one of
      (ii) fat attenuation index of epicardial adipose tissue ($FAI_{EpAT}$); and
      (iii) fat attenuation index of perivascular adipose tissue ($FAI_{PVAT}$);
      wherein $FAI_{PVAT}$ is determined using data gathered from a computer tomography (CT) scan along a length of a blood vessel; and
   (b) comparing each of the values determined in (a) to a pre-determined cut-off value or using the absolute value of each variable determined in (a) in order to generate an output value that indicates the patient's mortality risk or risk of suffering a cardiovascular event.

2. The method according to claim 1, wherein step (a) further comprises using the data gathered from a computer tomography scan along a length of a blood vessel to determine (iv) calcium index (Calcium-i) and/or (v) fibrous plaque index (FPi); wherein the value of (iv) and/or (v) is included in step (b) of claim 1.

3. The method according to claim 1, wherein step (a) further comprises using the data gathered from a computer tomography scan along a length of a blood vessel to determine (vi) perivascular water index (PVWi) and/or (vii) volumetric perivascular characterisation index (VPCI); wherein the value of (vi) and/or (vii) is included in step (b) of claim 1.

4. The method according to claim 1, further comprising determining one or more of (viii) age and (ix) gender of the patient and wherein the value of (viii) and/or (ix) is included in step (b) of claim 1.

5. The method according to claim 1, further comprising determining one or more of:
   (x) coronary calcium;
   (xi) hypertension;
   (xii) hyperlipidemia/hypercholesterolemia;
   (xiii) diabetes mellitus;
   (xiv) presence of coronary artery disease;
   (xv) smoking; and
   (xvi) family history of heart disease;

and wherein the value of one or more of (x)-(xvi) is included in step (b) of claim 1.

6. The method according to claim 1, further comprising determining one or more of:
(iv) calcium index (Calcium-i);
(v) fibrous plaque index (FPi);
(vi) perivascular water index (PVWi);
(vii) volumetric perivascular characterisation index (VPCI);
(viii) age of the patient;
(ix) gender of the patient;
(x) coronary calcium;
(xi) hypertension;
(xii) hyperlipidemia/hypercholesterolemia;
(xiii) diabetes mellitus;
(xiv) presence of coronary artery disease;
(xv) smoking; and
(xvi) family history of heart disease;
and wherein the value of one or more of (iv)-(xvi) is included in step (b) of claim 1.

7. The method according to claim 1, wherein coefficients for each of (i) to (iii) are derived from Cox hazard or logistic regression models.

8. The method according to claim 1, wherein the cut-off points for each of (i) to (v) are derived from receiver operating characteristic (ROC) curves.

9. The method according to claim 1, wherein the output value is a continuous single valued function or a value that falls within one of three discrete brackets corresponding to low, medium and high risk of a cardiac event, cardiac death or all-cause mortality.

10. The method according to claim 1, wherein the method is used to stratify patients according to their risk of all-cause or cardiac mortality.

11. The method according to claim 1, wherein the patient has been diagnosed with vascular inflammation, or a condition known to be associated with vascular inflammation.

* * * * *